United States Patent
Jia et al.

(10) Patent No.: US 11,806,379 B2
(45) Date of Patent: Nov. 7, 2023

(54) COMPOSITIONS, METHODS, AND MEDICAL COMPOSITIONS FOR TREATMENT OF AND MAINTAINING THE HEALTH OF THE LIVER

(71) Applicant: Unigen, Inc., Seattle, WA (US)

(72) Inventors: Qi Jia, Olympia, WA (US); Mesfin Yimam, Tacoma, WA (US); Ping Jiao, Newcastle, WA (US); Mei Feng Hong, Seattle, WA (US); Breanna Moore, Seattle, WA (US)

(73) Assignee: Unigen, Inc., Tacoma, WA (US)

( * ) Notice: Subject to any disclaimer, the term of this patent is extended or adjusted under 35 U.S.C. 154(b) by 353 days.

(21) Appl. No.: 15/208,934

(22) Filed: Jul. 13, 2016

(65) Prior Publication Data
US 2017/0035829 A1 Feb. 9, 2017

Related U.S. Application Data

(60) Provisional application No. 62/192,727, filed on Jul. 15, 2015.

(51) Int. Cl.
| | |
|---|---|
| *A61K 36/00* | (2006.01) |
| *A61K 36/79* | (2006.01) |
| *A61K 36/076* | (2006.01) |
| *A61K 36/185* | (2006.01) |
| *A61K 36/481* | (2006.01) |

(52) U.S. Cl.
CPC ............ *A61K 36/79* (2013.01); *A61K 36/076* (2013.01); *A61K 36/185* (2013.01); *A61K 36/481* (2013.01)

(58) Field of Classification Search
CPC ..... A61K 36/79; A61K 36/185; A61K 36/481
See application file for complete search history.

(56) References Cited

U.S. PATENT DOCUMENTS

| | | |
|---|---|---|
| 4,442,087 A | 4/1984 | Kojima et al. |
| 8,986,756 B2 | 3/2015 | Lee |

FOREIGN PATENT DOCUMENTS

| | | | |
|---|---|---|---|
| CN | 101053370 A | * | 10/2007 |
| CN | 101869603 | | 10/2010 |
| CN | 102058817 | | 5/2011 |
| CN | 103830714 A | * | 6/2014 |
| CN | 104353043 A | * | 2/2015 |
| KR | 100619498 | | 9/2006 |

OTHER PUBLICATIONS

Agyemang K, Han L, Liu E, Zhang Y, Wang T, Gao X. Recent Advances in Astragalus membranaceus Anti-Diabetic Research: Pharmacological Effects of Its Phytochemical Constituents. Evid Based Complement Alternat Med. 2013; 2013:654643.

Ajith TA, Hema U, Aswathy MS. Zingiber officinale Roscoe prevents acetaminophen-induced acute hepatotoxicity by enhancing hepatic antioxidant status. Food Chem. Toxicol. 2007; 45:2267-2272.

Albano E., Lott A.K., Slater T.F., Stier A., Symons M.C.R., and Tomasi A. (1982) Spin trapping studies on the free radical products formed by metabolic activation of carbon tetrachloride in rat liver microsomal fractions, isolated hepatocytes and in vivo. Biochem. J. 204:593-603.

Bajt ML, Cover C, Lemasters JJ, Jaeschke H. Nuclear translocation of endonuclease G and apoptosis-inducing factor during acetaminophen-induced liver cell injury. Toxicol. Sci. 2006; 94:217-225.

Bajt ML, Farhood A, Lemasters JJ, Jaeschke H. Mitochondrial bax translocation accelerates DNA fragmentation and cell necrosis in a murine model of acetaminophen hepatotoxicity. J. Pharmacol. Exp. Ther. 2008; 324:8-14.

Bajt ML, Ramachandran A, Yan HM, Lebofsky M, Farhood A, Lemasters JJ, Jaeschke H. Apoptosis-inducing factor modulates mitochondrial oxidant stress in acetaminophen hepatotoxicity. Toxicol. Sci. 2011; 122:598-605.

Carson EJ, Pruett SB: Development and characterization of a binge drinking model in mice for evaluation of the immunological effects of ethanol. Alcohol Clin Exp Res. 1996;20(1):132-8.

Cheng S1, Eliaz I, Lin J, Thyagarajan-Sahu A, Sliva D. Triterpenes from Poria cocos suppress growth and invasiveness of pancreatic cancer cells through the downregulation of MMP-7. Int J Oncol. 2013; 42(6):1869-74.

Cho WC1, Leung KN. In vitro and in vivo immunomodulating and immunorestorative effects of Astragalus membranaceus. J Ethnopharmacol. 2007; 113(1):132-41.

Colby, SR. Calculating Synergistic and Antagonistic Responses of Herbicide combinations. Weeds, vol. 15, No. 1 (Jan. 1967), pp. 20-22.

(Continued)

*Primary Examiner* — Qiuwen Mi

(74) *Attorney, Agent, or Firm* — Sandra Poteat Thompson; Finlayson Toffer

(57) ABSTRACT

Compositions and methods for treatment of and maintaining the health of the liver are disclosed that include a mixture of plant extracts, wherein the plant extracts comprise at least one *Myristica* extract, at least one *Astragalus* extract, and at least one *Schizandra* extract. Compositions and methods for treatment of and maintaining the health of the liver are disclosed that include a mixture of plant extracts, wherein the plant extracts comprise at least one *Myristica* extract enriched for one or more lignans, including phenylpropanoids, dimers and polymers, at least one *Astragalus* extract enriched for one or more polysaccharides and triterpenoids, and at least one *Schizandra* extract enriched for one or more lignans and organic acids. Compositions and methods for treatment of and maintaining the health of the liver are disclosed that include a mixture of plant extracts, wherein the plant extracts comprise at least one *Myristica* extract, at least one *Astragalus* extract, and at least one *Poria* extract.

13 Claims, 1 Drawing Sheet

(56) References Cited

OTHER PUBLICATIONS

Cover C, Mansouri A, Knight TR, Bajt ML, Lemasters JJ, Pessayre D, Jaeschke H. Peroxynitrite-induced mitochondrial and endonuclease-mediated nuclear DNA damage in acetaminophen hepatotoxicity. J. Pharmacol. Exp. Ther. 2005; 315:879-887.

Czaja M.J., Xu J., and Alt E. (1995) Prevention of carbon tetrachloride-induced rat liver injury by soluble tumor necrosis factor receptor. Gastroenterology 108:1849-1854.

Davern TJ 2nd, James LP, Hinson JA, Polson J, Larson AM, Fontana RJ, Lalani E, Munoz S, Shakil AO, Lee WM, Acute Liver Failure Study Group. Measurement of serum acetaminophen-protein adducts in patients with acute liver failure. Gastroenterology. 2006; 130:687-694.

Fu J, Wang Z, Huang L, Zheng S, Wang D, Chen S, Zhang H, Yang S. Review of the botanical characteristics, phytochemistry, and pharmacology of Astragalus membranaceus (Huangqi). Phytother Res. 2014; 28(9):1275-83.

Hanawa N, Shinohara M, Saberi B, Gaarde WA, Han D, Kaplowitz N. Role of JNK translocation to mitochondria leading to inhibition of mitochondria bioenergetics in acetaminophen-induced liver injury. J. Biol. Chem. 2008; 283:13565-13577.

Jaeschke H, Williams CD, McGill MR, Xie Y, Ramachandran A. Models of drug-induced liver injury for evaluation of phytotherapeutics and other natural products. Food Chem Toxicol. May 2013; 55:279-89.

James LP, Letzig L, Simpson PM, Capparelli E, Roberts DW, Hinson JA, Davern TJ, Lee WM. Pharmacokinetics of acetaminophen-protein adducts in adults with acetaminophen overdose and acute liver failure. Drug Metab. Dispos. 2009; 37:1779-1784.

Ji L, Jiang P, Lu B, Sheng Y, Wang X, Wang Z. Chlorogenic acid, a dietary polyphenol, protects acetaminophen-induced liver injury and its mechanism. J Nutr Biochem. 2013; 24(11):1911-9.

Kon K, Kim JS, Jaeschke H, Lemasters JJ. Mitochondrial permeability transition in acetaminopheninduced necrosis and apoptosis of cultured mouse hepatocytes. Hepatology. 2004; 40:1170-1179.

Larson AM. Acetaminophen hepatotoxicity. Clin. Liver Dis. 2007; 11:525-548.

Lee KY, Jeon YJ. Macrophage activation by polysaccharide isolated from Astragalus membranaceus. Int Immunopharmacol. 2005; 5(7-8):1225-33.

Lee SM, Lee YJ, Yoon JJ, Kang DG, Lee HS: Effect of Poria cocos on hypertonic stress-induced water channel expression and apoptosis in renal collecting duct cells. J Ethnopharmacol 2012, 141:368-376.

Liu W, Gao FF, Li Q, Lv JW, Wang Y, Hu PC, Xiang QM, Wei L. Protective effect of astragalus polysaccharides on liver injury induced by several different chemotherapeutics in mice. Asian Pac J Cancer Prev. 2014; 15(23):10413-20.

Loguidice A, Boelsterli UA. Acetaminophen overdose-induced liver injury in mice is mediated by peroxynitrite independently of the cyclophilin D-regulated permeability transition. Hepatology. 2011; 54:969-978.

Luckey SW and Petersen DR. (2001) Activation of Kupffer cells during the course of carbon tetrachloride-induced liver injury and fibrosis in rats. Exp. Mol. Pathol. 71:226-240.

Masubuchi Y, Suda C, Horie T. Involvement of mitochondrial permeability transition in acetaminophen-induced liver injury in mice. J. Hepatol. 2005; 42:110-116.

McGill MR, Sharpe MR, Williams CD, Taha M, Curry SC, Jaeschke H. The mechanism underlying acetaminophen-induced hepatotoxicity in humans and mice involves mitochondrial damage and nuclear DNA fragmentation. J. Clin. Invest. 2012a; 122:1574-1583.

McGill MR, Williams CD, Xie Y, Ramachandran A, Jaeschke H. Acetaminophen-induced liver injury in rats and mice: Comparison of protein adducts, mitochondrial dysfunction, and oxidative stress in the mechanism of toxicity. Toxicol. Appl. Pharmacol. 2012b; 264:387-394.

Morita T, Jinno K, Kawagishi H, Arimoto Y, Suganuma H, Inakuma T, et al. Hepatoprotective Effect of Myristicin from Nutmeg (*Myristica fragrans*) on Lipopolysaccharide / D-Galactosamine-Induced Liver Injury. J Agric Food Chem. 2003: 51:1560-5.

Nakagawa H, Maeda S, Hikiba Y, Ohmae T, Shibata W, Yanai A, Sakamoto K, Ogura K, Noguchi T, Karin M, Ichijo H, Omata M. Deletion of apoptosis signal-regulating kinase 1 attenuates acetaminophen-induced liver injury by inhibiting c-Jun N-terminal kinase activation. Gastroenterology. 2008; 135:1311-21.

PCT/US2016/042034, Search Report and Written Opinion, dated Oct. 25, 2016.

Young Sun Lee et al. "Effect of Astragali radix Extract on Acetaminophen-induced Hepatotoxicity in Mice", The Korean Association of Oriental Medical Physiology, Korean Intellectual Property Office, vol. 16, No. 4, Aug. 25, 2002, pp. 707-713.

Zhen-Lun Z. et al., "Hepatoprotective Effects of Astragalus root", Journal of Ethnopharmaology, vol. 30, No. 2, Sep. 1, 1990, pp. 145-149.

Rho Sook-Nyung et al. "Effect of Omija (*Schizandra chinensis* Baillon) Extracts on the Growth of Liver Cancer Cell Line SNU-398", Han'Guk Yongyang Hakhoe—Korean Journal of Nutrition, vol. 35, No. 2, Mar. 30, 2002, pp. 201-206.

Wan Y, Wu YL, Lian LH, Nan JX. Protective effect of Ornithogalum saundersiae Ait (Liliaceae) against acetaminophen-induced acute liver injury via CYP2E1 and HIF-1$\alpha$. Chin. J. Nat. Med. 2012; 10:177-184.

Mitchell JR, Jollow DJ, Potter WZ, Davis DC, Gillette JR, Brodie BB. Acetaminophen-induced hepatic necrosis. I. Role of drug metabolism. J. Pharmacol. Exp. Ther. 1973; 187:185-194.

Qiu Y, Benet LZ, Burlingame AL. Identification of hepatic protein targets of the reactive metabolites of the non-hepatotoxic regioisomer of acetaminophen, 3'-hydroxyacetanilide, in the mouse in vivo using two-dimensional gel electrophoresis and mass spectrometry. Adv. Exp. Med. Biol. 2001; 500:663-673.

Jaeschke H, McGill MR, Ramachandran A. Oxidant stress, mitochondria, and cell death mechanisms in drug-induced liver injury: lessons learned from acetaminophen hepatotoxicity. Drug Metab. Rev. 2012a; 44:88-106.

Jollow DJ, Mitchell JR, Potter WZ, Davis DC, Gillette JR, Brodie BB. Acetaminophen-induced hepatic necrosis. II. Role of covalent binding in vivo. J. Pharmacol. Exp. Ther. 1973; 187:195-202.

Jaeschke H. Glutathione disulfide formation and oxidant stress during acetaminophen-induced hepatotoxicity in mice in vivo: the protective effect of allopurinol. J. Pharmacol. Exp. Ther. 1990; 255:935-941.

Chamulitrat W., Jordan S.J., and Mason R.P. (1994) Nitric oxide production during endotoxic shock in carbon tetrachloride-treated rats. Mol. Pharmacol. 46:391-397.

Chamulitrat W., Blazka M.E., Jordan S.J., Luster M.I., and Mason R.P. (1995) Tumor necrosis factor-alpha and nitric oxide production in endotoxin-primed rats administered carbon tetrachloride. Life Sci. 57:2273-2280.

Cheeseman K.H., Davies M.J., Emery S., Maddix S.P., and Slater T.F. (1987) Effects of alpha-tocopherol on carbon tetrachloride metabolism in rat liver microsomes. Free Radic. Res. Commun. 3:325-330.

* cited by examiner

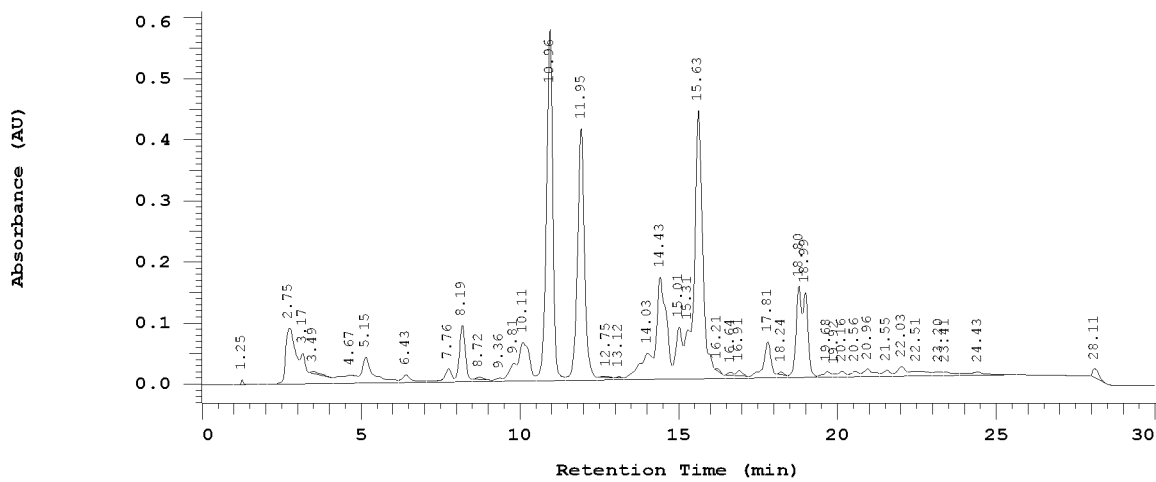
HPLC chromatogram of *Myristica fragrans* 70% ethanol extract

COMPOSITIONS, METHODS, AND MEDICAL COMPOSITIONS FOR TREATMENT OF AND MAINTAINING THE HEALTH OF THE LIVER

This United States Utility Application claims priority to U.S. Provisional Patent Application Ser. No. 62/192,727 filed on Jul. 15, 2015 and entitled "Compositions and Methods for Liver Health", which is commonly-owned and incorporated herein in its entirety by reference.

FIELD OF THE SUBJECT MATTER

The field of the subject matter is compounds and compositions useful for liver health management, including stereoisomers, pharmaceutically or nutraceutically acceptable salts, tautomers, glycosides and prodrugs of the disclosed compounds, compositions and related methods of improving and maintaining liver health.

BACKGROUND

The liver is a vital organ that plays a pivotal role in metabolism and detoxification of various endogenous and exogenous harmful substances. It is believed that more than 500 chemical reactions take place in the liver. Various xenobiotics or foreign chemical substances are known to cause hepatotoxicity, among which acetaminophen (n-acetyl-p-aminophenol or APAP) and carbon tetrachloride ($CCl_4$) are generally utilized to develop an animal model that mimics the human type of liver toxicity with similar mechanisms of actions. Ranges of biomarkers from serum or liver homogenates have been used to review and/or analyze the health status of the liver where a shift away from the normal range is considered an indication of insult to the organ. Among these biomarkers, the most frequently used are: ALT (alanine aminotransferase), AST (aspartate aminotransferase), MDA (malondialdehyde), GSH (glutathione), SOD (superoxide dismutase), c-Jun N-terminal kinase (JNK), GSH-Px (glutathione peroxidase), CAT (catalase), and TNF-alpha (tumor necrosis factor-alpha). Liver panels such as AST, ALT, total bilirubin, conjugated and unconjugated bilirubin, bile acid, total protein, albumin, globulin, and alkaline phosphatase have been used as a standard screen method for liver health. While ALT and AST are recognized as non-specific to liver injury, ALT has shown relative specificity to the liver. For example, AST has an origin ratio of liver (9000:1) vs muscle (5200:1); in comparison ALT has an origin ratio of liver (7600:1) vs muscle (750:1). The half-life of total AST and ALT are 17±5 hours and 47±10 hours, respectively. ALT is stable for 3 days at room temperature, 3 weeks in a refrigerator, 24 hours in whole blood; however, ALT deteriorates rapidly with repeated freezing and thawing. Serum ALT was used for efficacy screening of plant extracts in our studies.

APAP is a very safe and effective analgesic and antipyretic drug at therapeutic dosage. It is the most frequent cause of acute live failure in the United States. APAP-induced liver toxicity is clinically relevant, well studied, can be rapidly induced in vivo with a single dose, and has become a conventional model in assessing the potential hepatoprotective effects of phototherapeutics.

APAP-induced cell death is not caused by a single tragic event shutting down vital function of cells instead it induces a series of events beginning with the reactive metabolite formation and initiation of mitochondrial dysfunction, which is amplified through the JNK pathway, ultimately leading to non-functional mitochondria and massive DNA degradation leading to cell necrosis.

APAP toxicity takes place in very intricate pathways of mechanisms of actions. As previously established, the intracellular signaling mechanisms of APAP-induced cell death is initiated by the metabolism of a small fraction of the administered dose by P450 enzymes, mainly Cyp 2e1 and 1a2 (Zaher et al., 1998), to n-acetyl-p-benzoquinone imine (NAPQI). Under normal conditions, this highly reactive metabolite will be detoxified by GSH resulting in extensive hepatic GSH depletion (Mitchell et al., 197), which becomes critical at the time of overdose. Concurrently, an increasing amount of NAPQI reacts with protein sulfhydryl groups, causing the covalent adduction of cellular proteins (Jollow et al., 1973). Interestingly, studies have shown that the total protein binding in the cell is not as important as adducts in mitochondria (Tirmenstein and Nelson, 1989; Qiu et al., 2001). Mitochondrial protein binding triggers a mitochondrial oxidant stress (Jaeschke, 1990), which causes activation of apoptosis signal-regulating kinase 1 (Nakagawa et al., 2008) and c-Jun N-terminal kinase (JNK) (Hanawa et al., 2008) and the amplification of the mitochondrial oxidant stress and peroxynitrite formation by mitochondrial JNK translocation (Saito et al., 2010a). The extensive oxidant stress finally triggers the opening of the membrane permeability transition (MPT) pore in the mitochondria with collapse of the membrane potential (Kon et al., 2004; Masubuchi et al., 2005; Ramachandran et al., 2011a; Loguidice and Boelsterli, 2011) followed by the release of intermembrane proteins such as endonuclease G and apoptosis inducing factor (AIF) from mitochondria (Kon et al., 2004; Bajt et al., 2008). Both endonuclease G and AIF translocate to the nucleus and cause DNA fragmentation (Cover et al., 2005; Bajt et al., 2006, 2011) and ultimately cell death occurs. The collapse of the mitochondrial membrane potential with ATP depletion and the nuclear degradation are key events leading to cellular necrosis. Hence, there are multiple interference points where these mechanisms can be intercepted when designing therapeutic intervention for liver protection.

Knowing the chronology of the pathologic process of the model provides a guideline for therapeutic intervention. While oxidative stress and sterile inflammations play a significant role in APAP toxicity, pathophysiology of the model is characterized by a series of events, including metabolic activation between 0 and 2 h, depletion of GSH within the first 30 minutes, intracellular mechanisms of cell death between 2 and 12 h, an inflammatory response at time frame of 6-24 h, and regeneration in the timeframe of 24-72 h after APAP toxicity (Jaeschke et al., 2012a).

As mentioned, APAP overdose can cause severe liver toxicity in humans characterized by protein adduct formation (Davern et al., 2006; James et al., 2009), mitochondrial damage and nuclear DNA fragmentation (McGill et al., 2012a) that leads to cell death. Therefore, it is desirable to utilize animal models that could share similar pathophysiology features when testing plant extracts for liver protection. Thus, for in vivo experiments, the mouse is the preferred model, as the damage most closely resembles the human pathophysiology in both mechanism and dose-dependency. In fact, some suggest that the primary significant difference in APAP hepatotoxicity between mice and humans is the more delayed toxicity in humans which exhibits ALT peak at 24-48 h after exposure compared to mice when ALT peaks at 6-12 h (Larson, 2007). This difference may in part be explained because of differences in absorption between the two species. In contrast, the rat, although popular for natural product testing, is a poor model as most rat strains are largely insensitive to APAP toxicity (Mitchell et al., 1973; McGill et al., 2012b). Even at high dose of ≥1 g/kg, APAP mostly does not cause relevant liver injury (Jaeschke et al., 2013). And while GSH depletion and protein adducts can be measured, the lower adducts in rat liver mitochondria compared to mice appear to be insufficient to initiate enough mitochondrial dysfunction and subsequent amplification events to lead to necrotic cell death (McGill et al., 2012b). These fundamental differences between the two species have been reflected during evaluation of phytotherapeutics. For example, in a rat study, an APAP dose of 3 g/kg resulted in an increase of plasma ALT levels of about 3-fold compared to baseline and the phytotherapeutic attenuated this modest liver injury by 33% (Ajith et al., 2007). Any histological changes in this rat model were minimal and difficult to detect. On the other hand, in a mouse study, ALT increases were >60-fold of baseline after a 300 mg/kg APAP dose and the reduction by the phytotherapeutic was 75% (Wan et al., 2012). Histological changes caused by APAP toxicity and the protective effect of the drug were readily observed.

$CCl_4$, a halogenated alkane industrial chemical with restricted usage, is a well-known hepatotoxin that is widely used to induce acute toxic liver injury in a large range of laboratory animals. Humans have been exposed to $CCl_4$, in occupational surroundings and from environmental contamination, such as contaminated drinking water. Nevertheless, the chemical continues to provide an important service today as a model compound to elucidate the mechanisms of action of hepatotoxic effects such as fatty degeneration, fibrosis, hepatocellular death, and carcinogenicity (Slater 1981; Renner H. 1985; Reynolds 1963). It is considered as one of the classic chemically-induced liver toxicity animal models primarily associated with the formation of free radicals and lipid peroxidation.

Like APAP, $CCl_4$ toxicity is initiated by cytochrome P450s primarily of (CYP) 2E1, CYP2B1 or CYP2B2 (Nelson and Harrison, 1987), to yield reactive metabolic products trichloromethyl free radicals ($CCl_3-$), which can initiate lipid peroxidation and ultimately results in the overproduction of reactive oxygen species (ROS) and hepatocyte injuries (Poyer et al., 1980; Albano et al., 1982). In the process, these radicals can bind to cellular molecules (nucleic acid, protein, and lipid), impairing crucial cellular processes, such as lipid metabolism, with the potential outcome of fatty degeneration (steatosis) and direct damage to these macromolecules (Weddle et al., 1976). These radicals can also react with oxygen to form the trichloromethylperoxy radical $CCl_3OO-$, a highly reactive species. Once generated, it initiates the chain reaction of lipid peroxidation, which attacks and destroys polyunsaturated fatty acids, in particular those associated with phospholipids. This affects the permeability of mitochondrial, endoplasmic reticulum, and plasma membranes, resulting in the loss of cellular calcium sequestration and homeostasis, which can contribute heavily to subsequent cell damage. In this respect, antioxidants and radical scavengers have been used to study the mechanism of $CCl_4$ toxicity as well as to protect liver cells from $CCl_4$-induced damage by breaking the chain reaction of lipid peroxidation (Cheeseman et al., 1987). At the molecular level, $CCl_4$ activates TNF-α (Czaja et al., 1995), nitric oxide (NO) (Chamulitrat et al., 1994, 1995), and transforming growth factors (TGF) (Luckey et al., 2001) in the cell, processes that appear to direct the cell primarily toward destruction or fibrosis. These suggest that plant extracts with anti-inflammatory activity could have a potential application in liver protection. While acute administration of a large dose of $CCl_4$ causes severe necrosis, chronic administration of lower doses is frequently used to induce hepatic fibrosis.

Oxidative stress is an imbalance between the production of free radicals and the inherent capacity of the body to counteract or neutralize their harmful effects through interactions with various endogenous antioxidant defense networks. When there is a lack of an appropriate adaptation by the body antioxidant defense system, reactive oxygen species accumulation will lead to the activation of stress-sensitive intracellular signaling pathways that, in turn, promote cellular damage leading to necrosis. While damage of oxidative stress affects the whole body as a system, the impact becomes more detrimental when it involves vital organs, such as the liver, where primary detoxification takes place to remove and metabolize harmful toxins such as alcohol. As a result, the liver is susceptible to alcohol-induced injury as both alcohol and its primary metabolite acetaldehyde produce reactive oxygen species (ROS) and hydroxyl radicals (OH), altering hepatic antioxidant defense system. The most common pathological conditions such as fatty liver, hepatitis, fibrosis, and cirrhosis are observed in alcohol-linked liver disorders as a result of repeated exposure of alcohol. These outcomes in conjunction with cellular lipids, proteins, and DNA oxidation has been demonstrated in multiple experimental animals (Wu and Cederbaum, 2003). Here we used the most frequently used animal model with practical clinical implications, such as APAP, and confirmed findings with the classic $CCl_4$-induced hepatotoxicity model. Regardless of the chemical agents used to induce the hepatotoxicity, both the APAP and $CCl_4$ models share the critical step in oxidative stress induced by reactive oxygen species generated by excess intermediate metabolites leading to protein oxidation, lipid peroxidation, and DNA damage.

To this end, it would be desirable to develop, produce and utilize a composition, a compound, a medicinal composition and related methods that are designed to treat and maintain the health of the liver. Ideal compounds, medicinal compositions and compositions would be sufficient to effect treatment, including any one or more of: (1) treating or preventing damage of liver cells in a mammal; (2) promoting liver health; (3) preserve detoxification and anti-oxidation liver enzymes in a mammal; (4) increasing liver detoxification capacity in a mammal; (5) treating or preventing liver diseases in a mammal; (6) modifying inflammation of a liver in a mammal; and (7) improving liver renewal function. Ideal compounds and compositions can be derived from or comprise at least one plant extract, wherein the plant extract may or may not be enriched. As part of this development, it would be ideal to utilize frequently and acceptable models to test contemplated compounds and compositions. It would also be desirable to reliably design a therapeutic intervention for liver health by intercepting points in the mechanisms of liver degradation and studying those results.

SUMMARY OF THE SUBJECT MATTER

Compositions and methods for treatment of and maintaining the health of the liver are disclosed that include a mixture of plant extracts, wherein the plant extracts comprise at least one *Myristica* extract, at least one *Astragalus* extract, and at least one *Schizandra* extract.

Compositions and methods for treatment of and maintaining the health of the liver are disclosed that include a mixture of plant extracts, wherein the plant extracts comprise at least one *Myristica* extract enriched for one or more lignans, including phenylpropanoids, dimers and polymers, at least one *Astragalus* extract enriched for one or more polysaccharides and triterpenoids, and at least one *Schizandra* extract enriched for one or more lignans and organic acids.

Compositions and methods for treatment of and maintaining the health of the liver are disclosed that include a mixture of plant extracts, wherein the plant extracts comprise at least one *Myristica* extract, at least one *Astragalus* extract, and at least one *Poria* extract.

Compositions and methods for treatment of and maintaining the health of the liver are disclosed that include a mixture of plant extracts, wherein the plant extracts comprise at least one *Myristica* extract enriched for one or more lignans, including phenylpropanoids, dimers and polymers, at least one *Astragalus* extract enriched for one or more polysaccharides and triterpenoids, and at least one *Poria* extract enriched for one or more polysaccharides and triterpenoids.

Medical compositions for maintaining liver function, minimizing liver cell damage, promoting healthy liver, protecting liver antioxidation integrity, neutralizing toxins, diminishing the action of free radicals that affecting liver health, scavenging reactive oxygen species, reducing oxidative stress, preventing the formation of toxic metabolisms, improving liver detoxification capacity and/or function, liver cleansing, restoring liver structure, liver protecting liver cells from toxins, helping liver's blood flow and circulation, supporting liver function, fortifying and soothing lever, calming and tonifying liver, alleviating liver pain, purging harmful chemicals and organisms, supporting liver's metabolic process, alleviating liver discomfort, alleviating fatty liver, improving liver detoxification capacity, lowering liver enzymes, providing natural oxidants, increasing SOD, increasing GSH, reducing liver cell peroxidation, reducing fatty acid accumulation, maintaining healthy anti-inflammatory process, improving liver immune function, promoting liver cell regeneration, improving liver renewal function, simulating bile release, promoting healthy bile flow, preventing treating and managing alcohol hangover and symptoms related to overdose of chemicals, drugs and prescription medicines, liver rejuvenating, or the like of a mammal are also disclosed, wherein the medical composition contains contemplated compositions as an effective ingredient.

BRIEF DESCRIPTION OF THE FIGURES

FIG. 1 shows a HPLC chromatogram of *Myristica fragrans* 70% ethanol extract

DETAILED DESCRIPTION

In brief, the present disclosure is directed to compounds and compositions useful for liver health management, including stereoisomers, pharmaceutically or nutraceutically acceptable salts, tautomers, glycosides and prodrugs of the disclosed compounds, and to related methods of improving liver health.

Contemplated compounds and compositions are derived from or comprise at least one plant extract, wherein the plant extract may or may not be enriched. As part of this development, frequently and acceptable models were utilized to test contemplated compounds and compositions. In addition, a therapeutic intervention for liver health was designed by intercepting points in the mechanisms of liver degradation and studying those results. Contemplated compounds, medicinal compositions and compositions are sufficient to effect treatment, including any one or more of: (1) treating or preventing damage of liver cells in a mammal; (2) promoting liver health; (3) preserve detoxification and anti-oxidation liver enzymes in a mammal; (4) increasing liver detoxification capacity in a mammal; (5) treating or preventing liver diseases in a mammal; (6) modifying inflammation of a liver in a mammal; and (7) improving liver renewal function.

Compositions and methods for treatment of and maintaining the health of the liver are disclosed that include a mixture of plant extracts, wherein the plant extracts comprise at least one *Myristica* extract, at least one *Astragalus* extract, and at least one *Schizandra* extract.

Compositions and methods for treatment of and maintaining the health of the liver are disclosed that include a mixture of plant extracts, wherein the plant extracts comprise at least one *Myristica* extract enriched for one or more lignans, including phenylpropanoids, dimers and polymers, at least one *Astragalus* extract enriched for one or more polysaccharides and triterpenoids, and at least one *Schizandra* extract enriched for one or more lignans and organic acids.

Compositions and methods for treatment of and maintaining the health of the liver are disclosed that include a mixture of plant extracts, wherein the plant extracts comprise at least one *Myristica* extract, at least one *Astragalus* extract, and at least one *Poria* extract.

Compositions and methods for treatment of and maintaining the health of the liver are disclosed that include a mixture of plant extracts, wherein the plant extracts comprise at least one *Myristica* extract enriched for one or more lignans, including phenylpropanoids, dimers and polymers, at least one *Astragalus* extract enriched for one or more polysaccharides and triterpenoids, and at least one *Poria* extract enriched for one or more polysaccharides and triterpenoids.

Medical compositions for maintaining liver function, minimizing liver cell damage, promoting healthy liver, protecting liver antioxidation integrity, neutralizing toxins, diminishing the action of free radicals that affecting liver health, scavenging reactive oxygen species, reducing oxidative stress, preventing the formation of toxic metabolisms, improving liver detoxification capacity and/or function, liver cleansing, restoring liver structure, liver protecting liver cells from toxins, helping liver's blood flow and circulation, supporting liver function, fortifying and soothing lever, calming and tonifying liver, alleviating liver pain, purging harmful chemicals and organisms, supporting liver's metabolic process, alleviating liver discomfort, alleviating fatty liver, improving liver detoxification capacity, lowering liver enzymes, providing natural oxidants, increasing SOD, increasing GSH, reducing liver cell peroxidation, reducing fatty acid accumulation, maintaining healthy anti-inflammatory process, improving liver immune function, promoting liver cell regeneration, improving liver renewal function, simulating bile release, promoting healthy bile flow, preventing treating and managing alcohol hangover and symptoms related to overdose of chemicals, drugs and prescription medicines, liver rejuvenating, or the like of a mammal are also disclosed, wherein the medical composition contains contemplated compositions as an effective ingredient.

In contemplated embodiments, compositions, compounds or medicinal compositions may be used to help alleviate or aid at least one liver disorder, wherein the liver disorder comprises viral hepatitis, alcohol hepatitis, autoimmune hepatitis, alcohol liver disease, fatty liver disease, steatosis, steatohepatitis, non-alcohol fatty liver disease, drug-induced liver disease, cirrhosis, fibrosis, liver failure, drug induced liver failure, metabolic syndrome, hepatocellular carcinoma, cholangiocarcinoma, primary biliary cirrhosis, bile capillaries, Gilbert's syndrome, jaundice, or any other liver toxicity associated indication, and generally with acceptable toxicity to a patient or any other liver associated indication or any combination thereof.

In the process, it was observed that some plant extracts showed a reduction in serum ALT only in one model and hence a criteria was set that for a lead to be considered as a true hit must show efficacy in both models. This benchmark helped to narrow down the number of positive hits from the screening. In this process, *Myristica, Astragalus, Schisandra, Poria* and *Artemisia* were selected because of their significant and reproducible efficacy in both models.

*Myristica fragrans*, belonging to the Myristicaceae family, is the important source of the spices nutmeg and mace, a well-known medicinal herbal medicine as well. It is widely grown across the tropical countries such as Indonesia, Malaysia, Guangdong and Yunnan in China, Grenada in the Caribbean, Kerala in India, Sri Lanka and South America countries, possessing variety of pharmacological properties including anti-diarrhea, anti-omitting, soothing stomach pain, analgesic, hypnotic, neuroprotective and appetite stimulating.

The aromatic oil is a key active ingredient of this herbal medicine. The main chemical constituents of *Myristica fragrans* are myristicin, myristic acid, elemicin, saffrole, eugenol, palmitic, oleic, lauric and other acids. The essential oil could be utilized as a flavoring or in perfume, and it is also useful in treatment of paralysis and rheumatism. Myristicin, one of the major constituents of essential oil, was reported with potent hepatoprotective activity in the lipopolysaccharide/D-galactosamine-induced liver injury model. Myristicin also possess potent anti-fungal, antioxidant anti-inflammatory properties.

*Astragalus membranaceus* root is one popular Chinese herb from the Fabaceae family (legumes), with the common name *Radix Astragali, Astragalus* root, or huangqi (in Chinese). Huangqi is one of the 50 fundamental herbs used in traditional Chinese medicine and was included in many TCM preparations with a wide range of biological functions. It was originally described as an herb that is sweet, is slightly worm-like in nature, functions as a tonic and diuretic, alleviates disorders of the lungs and chest, nourishes qi and blood, and treats hemorrhoids. It has been recently studied as treatment for cardiovascular disorders, hepatitis, kidney disease, and diabetes. The root extract of *Astragalus* was reported with protective effect against the liver damage produced by carbon tetrachloride ($CCl_4$) in animals.

The primary active ingredients in the extract of *Radix Astragali* are flavonoids, saponins, and polysaccharides. Flavonoids, primarily isoflavons, act as antioxidants, which are beneficial to the circulations and soothing the gastrointestinal system. Among over 40 saponins reported from *Radix Astragali*, astragaloside was identified as the major marker compound with broad pharmacological activities involved in cardiovascular, immune, digestive, nervous, and cancer diseases. The polysaccharides of *Radix Astragali*, called astragalans, were found in relatively high content in the roots. Polysaccharides content in commercial *Astragalus* extracts could be standardized to the customized level from 10% to 90%. The immunomodulatory effect of the *Radix Astragali* has been attributed to its polysaccharides especially for radiation and chemotherapy patients in cancer treatments. *Astragalus* polysaccharides were also reported with anti-inflammation, anti-tumor, and hepatoprotecive activity in different studies.

*Poria cocos wolf*, a fungus in the family Polyporaceae, is medicinal mushroom growing on the roots of Chinese red pine trees or other conifer trees, with common names as fuling (茯苓) in China, and matsuhodo in Japan and is also known as hoelen, *poria*, tuckahoe, or China root. Its Latin nomenclature has been revised several times, with *Woffiporia extensa* as the currently botanical name. Fuling, as one of the chief ingredients in TCM, has been included in many ancient decoctions and formulas, which are still widely used even today, such as the fuling five formula, four major herbs combination, cinnamon and Fuling formula, etc. The properties of fuling include acting as a diuretic, a sedative and a tonic. Traditional uses of fuling includes treating nausea, vomiting, diarrhea, loss of appetite, stomach ulcer as well as insomnia and amnesia. Many biological activities have been reported for this fungus or fungal extracts, including anti-microbial, anti-fungal, antioxidant, neuroprotective, anti-inflammatory, anti-angiogenic and anti-cancer efficacy. The mechanism of the antiinflammation of *P. cocos* ethanol extracts is demonstrated as via inhibition of iNOS, COX-2, IL-1β, and TNF-α through inactivation of the NF-κB signaling pathway in lipopolysaccaride (LPS)-stimulated RAW 264.7 macrophages. The inhibitory effects of *Poria cocos* on the secretion of different cytokines from human peripheral blood monocytes have also been reported.

A major constituent of fuling is polysaccharides (Pachyman) in the form of β-glucan, which is 91-98% of the dried fungal fruit body. Variable biological functions have been reported for *poria cocos* polysaccharides, such as antioxidant, anti-hyperglycemic, soothing the stomach pain, anti-inflammation, anti-cancer and immunological modulation. Polysaccharides were reported with anti-tumor activities against different cancer lines both in vivo and in vitro. Triterpenoids were also identified as active components in fuling, which are actively researched, mainly on anti-cancer, anti-inflammatory efficacies, and potential immunological activity as well. Although the mechanism of anti-inflammatory of *poria cocos* is not fully understood, phospholipase A enzyme inhibition has been confirmed by several studies.

*Artemisia capillaris*, with the common name "yinchen' or "yinchenhao" in Chinese depending on the different collection season, also known as "yinjin" in Korean, is one of the commonly used TCM included in various ancient Chinese dispensatories. The earliest record of *Artemisia capillaris* was recorded in Shen Nong Ben Cao Jing (The Classic of Herbal Medicine)—a Chinese book on agriculture and medicinal plants—for treating jaundice, removing the dampness, and as a diuretic. Both aqueous extracts and ethanol extracts have been reported as having hepatoprotective efficacy in both in vitro assays and in vivo animal studies. Catechins, coumarins, flavonoids, organic acids, water soluble polysaccharides, and polypeptides have been reported as active components responsible for the liver protective activities of *Artemisia capillaris*.

*Myristica* extract is a contemplated component or constituent that can be utilized as part of a target compound or composition. *Myristica* extract may be obtained from any suitable source, including *M. alba, M. ampliata, M. andamanica, M. arfakensis, M. argentea, M. atrescens, M. basilanica, M. brachypoda, M. brevistipes, M. buchneriana, M. byssacea, M. ceylanica M. cinnamomea, M. coacta, M. colinridsdalei, M. conspersa, M. corticata, M. crassa, M. dactyloides, M. dasycarpa, M. depressa, M. devogelii, M. elliptica, M. extensa, M. fasciculata, M. filipes, M. fissurata,*

*M. flavovirens, M. frugifera, M. gigantea, M. gillespieana, M. globosa, M. hollrungii, M. inaequalis, M. incredibilis, M. iners, M. inundata, M. irya, M. kalkmanii, M. kjellbergii, M. lasiocarpa, M. leptophylla, M. longipetiolata, M. lowiana, M. macrantha, M. magnifica, M. magnifica, M. maingayi, M. malabarica, M. malabarica, M. maxima, M. mediterranea, M. millepunctata, M. nana, M. olivacea, M. ornata, M. ovicarpa, M. pachycarpidia, M. papillatifolia, M. perlaevis, M. petiolata, M. philippensis, M. pilosella, M. pilosigemma, M. polyantha, M. psilocarpa, M. pubicarpa, M. pygmaea, M. robusta, M. sangowoensis, M. sarcantha, M. schlechteri, M. simulans, M. sinclairii, M. sogeriensis, M. succadanea, M. tamrauensis, M. teijsmannii, M. trianthera, M. ultrabasica, M. verruculosa, M. yunnanensis* and other myristicin enriched plants anise seed (*Pimpinella anisum, Pimpinella vulgare, Illicium anisatum, Illicium verum*), Parsley (*Petroselinum crispum*), dill (*Anethum graveolen*), ligusticum (*ligusticum sinense Oliv.* and *L. jeholense*), Queen Anne's lace (*Daucus carota L.* subsp. *carota*), carrot (*Daucus carota L.* subsp. *sativus* (Hoffm.) Arcang.) or any combination thereof.

In some embodiments, a contemplated *Myristica* extract comprises about 0.01% to about 99.9% phenylpropanoids or lignan dimers and polymers. In contemplated embodiments, the extract may be extracted by utilizing water, ethanol, methanol, alcohol, mixed water solvents or combinations thereof.

As contemplated, suitable lignans comprise Safrole, Isomyristicin, 1-(3,4,5-Trihydroxyphenyl)-2-propene 1,2-Methylene, 3-Me ether, Anthriscinol, 4-Allylsyringol, Anthriscinol, 3-(3-Methoxy-4,5-methylenedioxyphenyl)-2-propen-1-ol, Elemicin, Isoelemicin, 3',4',5'-Trimethoxycinnamyl alcohol, 3'-Methoxy-4',5-methylenedioxycinnamyl alcohol, Methoxyeugenol, Parakmerin A, 4,7'-Epoxy-3,8'-bilign-7-ene-3',4',5-triol 5-mether, Otobain, Cagayanin, Austrobailignan 5, 1,2-Dihydrodehydroguaiaretic acid, Dehydrodiisoeugenol, Isodihydrocarinatidin, Isolicarin A, Otobaphenol, Macelignan, 3',4,4',5-Tetrahydroxy-3,8'-bilign-8-ene, Guaiacin, Dihydroguaiaretic acid, 5-[3-(4-Hydroxy-3-methoxyphenyl)-1,2-dimethylpropyl]-3-methoxy-1,2-benzenediol, Otobanone, Cagayanone, Zuihonin B, 3,4:3',4'-Bis(methylenedioxy)-7,7'-epoxylignan, Hydroxyotobain, Isogalcatin, Austrobailignan 7, Machilin F, 7-Hydroxyaustrobailignan 5, Saururinol, 2-(4-Allyl-2-methoxyphenoxy)-1-(4-hydroxy-3-methoxyphenyl)-1-propanol, Fragransin A2, Nectandrin B, Myristargenol A, Myristargenol B, 2,3-Dihydro-7-methoxy-2-(3-methoxy-4,5-methylenedioxyphenyl)-3-methyl-5-(1-propeyl)benzofuran, Fragransol C, Fragransol D, 2-(4-Allyl-2,6-dimethoxyphenoxy)-1-(3,4-methylenedioxyphenyl)-1-propanol, 2-(4-Allyl-2,6-dimethoxyphenoxy)-1-(4-hydroxy-3-methoxyphenyl)-1-propanol, Fragransin C2, Fragransin C3b, Fragransin C3a, Fragransin C1, Fragransol A, Myrisisolignan, 2-(4-Allyl-2,6-dimethoxyphenoxy)-1-(3,4-dimethoxyphenyl)-1-propanol, Fragransin D3, Fragransin D2, Fragransin D1, Virolongin B, 2-(4-Allyl-2,6-dimethoxyphenoxy)-1-(3-hydroxy-4,5-dimethoxyphenyl)-1-propanol, Fragransin B2, Fragransin B3, Fragransin B1, Myristicanol B, 3,4-Methylene, 3',5'-di-Me ether, Ac, 2-(4-Allyl-2,6-dimethoxyphenoxy)-1-(3,4,5-trimethoxyphenyl)-1-propanol, Myristicanol A, 3,4-Methylene, 3',5'-di-Me ether, benzoyl, Argenteane, or any combination thereof.

*Astragalus* extract is a contemplated component or constituent that can be utilized as part of a target compound or composition. *Asragalus* extract may be obtained from any suitable source, including *A. mongholius, A. tongolensis, A.tibetanus, A. camptodontus, A. aksusis, A. floridus, A. chrysopterus, A. maowenensis, A. yunnanensis Franch., A. ernestii Comb, Hedysarum polybotrys, A. pubiflorus, Medicago sativa L., Melilotus suaveolens Ledeb., Melilotus albus Desr., Caragana sinica, Oxytropis caerulea, Oxytropis glabra, Dunbaria villosa Makino, Malva rotundifolia L., Althaea officinalis*, or any combination thereof. Contemplated extracts may comprise 0.01% to about 100% polysaccharides and about 0.01% to about 100% triterpenoids.

In some embodiments, contemplated triterpenoids may comprise at least one suitable triterpenoid, including Askendoside A, Acetylastragaloside I, Agroastragaloside I, Agroastragaloside II, Agroastragaloside III, Agroastragaloside IV, Agroastragaloside V, Alexandroside I, Armatoside I, Armatoside II, Asernestioside A, Asernestioside B, Asernestioside C, Askendoside B, Askendoside C, Askendoside D, Askendoside F, Askendoside G, Askendoside K, Astrachrysoside A, Astragaloside I, Astragaloside II, Astragaloside III, Astragaloside IV, Astragaloside V, Astragaloside VI, Astragaloside VII, Astragenol, Astramembrangenin, Astramembrannin II, Astramembranoside A, Astramembranoside B, Astrasieversianin I, Astrasieversianin II, Astrasieversianin III, Astrasieversianin IX, Astrasieversianin V, Astrasieversianin XI, Astrasieversianin XII, Astrasieversianin XIII, Astrasieversianin XV, Astraverrucin I, Astraverrucin II, Astraverrucin III, Astraverrucin IV, Astraverrucin V, Astraverrucin VI, Astraverrucin VII, Astrojanoside A, Azukisaponin II, Baibutoside, Bicusposide A, Bicusposide B, Bicusposide C, Bicusposide D, Bicusposide E, Bicusposide F, Brachyoside A, Brachyoside B, Brachyoside C, Caspicuside I, Caspicuside II, Cephalotoside A, Ciceroside A, Ciceroside B, Cloversaponin IV, Complanatin, Cycloadsurgenin, Cycloalpigenin, Cycloalpigenin A, Cycloalpigenin B, Cycloalpigenin C, Cycloalpioside, Cycloalpioside A, Cycloalpioside B, Cycloalpioside C, Cycloalpioside D, Cycloaraloside B, Cycloaraloside C, Cycloaraloside D, Cycloaraloside E, Cycloaraloside F, Cycloascauloside A, Cycloascauloside B, Cycloascidoside A, Cycloasgenin A, Cycloasgenin B, Cycloasgenin C, Cyclocanthogenin, Cyclocanthoside A, Cyclocanthoside B, Cyclocanthoside C, Cyclocanthoside D, Cyclocanthoside E, Cyclocanthoside F, Cyclocanthoside G, Cyclocarposide, Cyclocarposide A, Cyclocarposide B, Cyclocarposide C, Cyclocephalogenin, Cyclocephaloside I, Cyclocephaloside II, Cyclochivinoside B, Cyclochivinoside C, Cyclochivinoside D, Cyclodissectoside, Cycloexoside, Cyclogaleginoside A, Cyclogaleginoside B, Cyclogaleginoside D, Cyclogaleginoside E, Cyclogalgeginin, Cycloglobiceposide A, Cycloglobiceposide B, Cycloglobiseposide C, Cyclomacrogenin B, Cyclomacroside A, Cyclomacroside B, Cyclomacroside C, Cyclomacroside D, Cyclomacroside E, Cycloorbicoside A, Cycloorbicoside B, Cycloorbicoside C, Cycloorbicoside D, Cycloorbigenin, Cycloorbigenin A, Cycloorbigenin B, Cycloorbigenin C, Cyclopycnanthogenin, Cyclosieversioside C, Cyclosieversioside H, Cyclosiversioside E, Cyclostipuloside A, Cyclostipuloside B, Cyclotrisectoside, Cyclounifolioside A, Cyclounifolioside B, Cyclounifolioside D, Dasyanthogenin, Dihydrocycloorbigenin A, Elongatoside, Eremophiloside A, Eremophiloside B, Eremophiloside C, Eremophiloside D, Eremophiloside E, Eremophiloside F, remophiloside G, Eremophiloside H, Eremophiloside I, Eremophiloside J, Eremophiloside K, Hareftoside C, Hareftoside D, Hareftoside E, Hispidacin, Huangqiyegenin I, Huangqiyenin A, Huangqiyenin B, Huangqiyenin D, Huangqiyenin E, Huangqiyenin F, Huangqiyenin G, Huangqiyenin H, Huangqiyenin I, Huangqiyenin J, Isoastragaloside I, Isoastragaloside II, Isoastragaloside IV, Isocomplanatin, Kahiricoside I, Kahiricoside II, Kahiricoside III, Kahiricoside IV, Kahiricoside V, Macrophyllosaponin A, Macrophyllosaponin B, Macrophyllosaponin C, Macrophyllosaponin D, Macrophyllosaponin E, Malonylastragaloside I, Mongholicoside A, Mongholicoside B, Mongholicoside I, Mongholicoside II, Oleifolioside A, Oleifolioside B, Orbicoside, Orbigenin, Prusianoside A, Prusianoside B, Quisquagenin, Quisvaloside B, Rubixanthin, almitate, Rubixanthin, Sapogenin A, Sapogenin III, Secomacrogenin B, Sieberoside I, Sieberoside II, Soyasapogenol B, Tomentoside I, Tomentoside II, Trigonoside I, Trigonoside III, Trojanoside A, Trojanoside B, Trojanoside C, Trojanoside D, Trojanoside E, Trojanoside F, Trojanoside I, Trojanoside J, Astragaloside VIII, 11-p-Coumaroylnepeticin or any combination thereof.

Poria extract is a contemplated component or constituent that can be utilized as part of a target compound or composition. Poria extract may be obtained from any suitable source, including polypore mushrooms, *Agaricus subrufescens, Agaricus blazei, Antrodia camphorate, Boletus edulis, Coriolus pargamenus, Coriolus heteromorphus, Crytoderma citrinum, Flammulina velutiper, Formitopsis cytisina, Formitopsis. pinicola, Ganoderma lucidum, Ganoderma sinense, Ganoderma tsugae, Gloephyllum saepiarium, Grifola frondosa, Hericium erinaceus, Hydnellum peckii, Lentinus edodes, Microporus flabelliformis, Morchella esculenta, Ophiocordyceps sinensi, Piptororus betulinus, Pleurotus nebrodensis, Polyporus umbeilatus, Polyporus tuberaster, Poria cocos, Schizophyllum commune, Skeletocutis vulgaris, Trametes gibbosa, Trametes versicolor (Coriolus versicolor), Ustilago maydis*, or any combination thereof. Contemplated extracts may comprise 0.01% to about 100% polysaccharides and about 0.01% to about 100% triterpenoids.

In some embodiments, contemplated triterpenoids isolated from Poria extract may comprise at least one suitable triterpenoid, including 25-Hydroxypachymic acid, 25-Hydroxy-3-epitumulosic acid, 16,25-Dihydroxyeburiconic acid, 3,16,25-Trihydroxy-24-methylenelanosta-7,9(11)-dien-21-oic acid, 16,25-D ihydroxydehydroeburicoic acid, 15-Hydroxydehydrotumulosic acid, 6-Hydroxydehydropachymic acid, 3,16,26-Trihydroxylanosta-7,9(11),24-trien-21-oic acid, 3,4-Secolanosta-4(28),7,9(11),24-tetraene-3, 26-dioic acid; (24Z)-form, Pregn-7-ene-3,11,15,20-tetrol, Poricoic acid DM, 26-Hydroxyporicoic acid DM, Poricoic acid D, Poricoic acid CM, Poricoic acid C; 25-Hydroxy, Poricoic acid CE, Poricoic acid C, Poricoic acid BM, Poricoic acid B; Deoxy Poricoic acid B, Eburicodiol, Poricoic acid G, Poricoic acid GM, Poricoic acid A, Poricoic acid AM, Poricoic acid AE, 25-Methoxyporicoic acid A, Poricoic acid H, 25-Hydroxyporicoic acid H, Poricoic acid HM, 6,7-Dehydroporicoic acid H, Dehydroeburicolic acid, 3-Hydroxylanosta-7,9(11),24-trien-21-oic acid, 5,8-Epidioxy-3,16-dihydroxy-24-methylenelanosta-6,9(11)-dien-21-oic acid, Poricoic acid E, Poriacosone A, Poriacosone B, Poricoic acid F, 29-Hydroxypolyporenic acid C, 29-Hydroxydehydrotumulosic acid, 29-Hydroxydehydropachymic acid, Pachymic acid, Acetylpachymic acid, Dehydropachymic acid, 3,16-Dihydroxy-24-methylenelanosta-7,9(11)-dien-21-oic acid; 3-O-(4-Hydroxybenzoyl), 3-Epidehydrotumulosic acid, 3-Epidehydropachymic acid, 3,16-Dihydroxylanosta-7,9(11),24-trien-21-oic acid, 16-Hydroxytrametenoic acid, 3,16-Dihydroxylanosta-8,24-dien-21-oic acid or any combination thereof.

Artemisia extract is a contemplated component or constituent that can be utilized as part of a target compound or composition. Artemisia extract may be obtained from any suitable source, including *Artemisia absinthium, Artemisia abrotanum L., Artemisia afra, Artemisia annua L, Artemisia arborescens, Artemisia asiatica, Artemisia campestris, Artemisia deserti, Artemisia iwayomogi, Artemisia ludoviciana, Artemisia vulgaris, Artemisia oelandica, Artemisia princeps Pamp, Artemisia sacrorum, Artemisia scoparia, Artemisia stelleriana, Artemisia frigida Willd, Artemisia anethoides Mattf., Artemisia anethifolia Weber., Artemisia faurier Nakai, Origanum vulgare, Siphenostegia chinensis*, or any combination thereof.

Artemisia extract may be enriched for one or more biopolymers, as contemplated herein. Contemplated polymers and biopolymers isolated from Artemisia extract are extracted with any suitable solvent, including water, methanol, ethanol, alcohol, a water-mixed solvent or a combination thereof. In contemplated embodiments, the Artemisia extract comprises about 0.01% to about 99.9% biopolymers with individual or a median molecular weights higher than about 500 g/mol. In some contemplated embodiments, the Artemisia extract comprises about 0.01% to about 99.9% biopolymers with individual or a median molecular weights higher than about 750 g/mol. In other contemplated embodiments, the Artemisia extract comprises about 0.01% to about 99.9% biopolymers with individual or a median molecular weights higher than about 1000 g/mol.

Schisandra chinensis, also known as Wuweizi and Wurenchum, is traditionally used for conditions of lung and kidney insufficiency. It is also indicated in cases of chronic cough and dyspnea, diarrhea, night sweats, wasting disorders, irritability, palpitations and insomnia, as well as a general tonic for treating fatigue associated with illness. In modern pharmacotherapy, mounting experimental and clinical evidences suggest the hepatoprotective nature of Schizandra extracts preventing carbon tetrachloride-induced hepatotoxicity, glutathione depletion and stimulated the activity of glutathione reductase. The major active principles of Schizandra are lignans called Schizandrins, which have energizing properties by increasing the activity of some enzymes which participate in the oxidative phosphorylation process, also increased superoxide dismutase and catalase activities in rat liver cytosol and were able to inhibit gossypol-induced superoxide anion generation in rat liver microsomes. The hepatoprotective effects of Schisandra fruit extracts has been reported in Chinese literature with patients with hepatitis, in a clinically controlled trial resulted in 68% (72/107) and 44% (36/72) improvement in serum ALT levels within 4 weeks and 8 weeks.

Schizandra extract is a contemplated component or constituent that can be utilized as part of a target compound or composition. Schizandra extract may be obtained from any suitable source, including *Schisandra chinensis, Schisandra elongate, Schisandra glabra, Schisandra glaucescens, Schisandra henryi, Schisandra incarnate, Schisandra lancifolia, Schisandra neglecta, Schisandra nigra, Schisandra propinqua, Schisandra pubescens, Schisandra repanda, Schisandra rubriflora, Schisandra rubrifolia, Schisandra sinensis, Schisandra sphaerandra, Schisandra sphenanthera, Schisandra tomentella, Schisandra tuberculata, Schisandra vestita, Schisandra viridis, Schisandra wilsoniana* or a combination thereof.

Schizandra extract may be enriched for one or more lignans and organic acids, as contemplated herein. Contemplated lignans isolated from Schizandra extract is Schisandrin, Deoxyschizandrin, γ-Schizandrin, Pseudo-γ-schizandrin, Wuweizisu B, Wuweizisu C, Isoschizandrin, Pregomisin, eoschizandrin, Schizandrol, Schizandrol A, Schizandrol B, Schisantherin A, B, C, D, E, Rubschisantherin, Schisanhenol acetdte, Schisanhenol B, Schisanhenol, Gomisin A, B, C, D, E, F, G, H, J, N, O, R, S, T, U, Epigomisin O, Angeloylgomisin H, O, Q, T, igloylgomisin H, P, Angeloyisogomisin O, Benzoyl-gomisin H, O, P, Q, Benzoyl-isogomisin or a combination thereof. Contemplated organic acids isolated from a *Schizandra* extract include malic acid, citric acid, shikimic acid or a combination thereof.

Therefore, for practical application, the idea of discovering a special blend with enhanced efficacy to protect liver from repeated exposures of oxidative stress was conceived keeping alcohol-induced liver injury, generalized fatigue and exhaustion in mind. Historically, some botanicals have been reported to be associated with anti-oxidative actions in biological systems, acting as scavengers of free radicals rendering their usage in herbal medicine for various human ailments. In contemplated embodiments, plant materials with historical liver associated efficacy and safety data were combined and considered to give a beneficial boost in their indication for overall liver health.

Contemplated materials and constituents demonstrated different degree of inhibitions. Extracts from *Myristica* seemed to show higher protection of liver injury caused by acetaminophen (up to 94.4% at a dose of 400 mg/kg), at higher dosage (i.e. 500 mg/kg) the extract showed only 37.6% inhibitions in carbon tetrachloride induced hepatotoxicity model. Similarly, *Astragalus* showed statistically non-significant 50.6% inhibitions in serum ALT in the acetaminophen model, whereas in the carbon tetrachloride induced hepatotoxicity model, statistically significant 34.1% reductions in serum ALT was documented. On the other hand, *Schisandra* showed 47.6% reduction in serum ALT level at the dose of 400 mg/kg in carbon tetrachloride-induced hepatotoxicity model; in contrast, at higher dose such as 500 mg/kg, the inhibitions observed in the acetaminophen-induced liver injury model was 41.4%, when compared to vehicle control. *Poria* and *Artemisia* showed similar and moderate liver protection activity in both models. Given these strong individual performances observed in a separate model for each plant, the idea of combining these plant extracts for a better outcome in both models was reinforced. Previous studies have attested the antioxidant activities of individual plant materials *Myristica* ("M"), *Astragalus* ("A"), *Schisandra* ("S"), and *Poria* ("P") with various degrees of liver protection abilities. However, they were never been combined together before at specific ratios to yield compositions designated as "MAP" (*Myristica, Astragalus* and *Poria*) or "MAS" (*Myristica, Astragalus* and *Schisandra*).

Contemplated compositions were initially formulated by developing leads in specific ratios such as 1:1, 1:2, 2:1, 1:4 and 4:1 using the $CCl_4$-induced hepatotoxicity model. Because of its high degree of serum ALT inhibition, *Myristica fragrance* was selected as a major component to be paired with each plant material (*Schisandra chinensis, Artemisia capillaris, Astragalus membranaceus* or *Poria cocos*) for the disclosed ratios in $CCl_4$ model and tested at a dose of 400 mg/kg. Various degrees of statistically significant inhibitions in serum ALT, and hence presumed liver protection from the injury, were observed for all the ratios when *Myristica fragrance* was formulated with *Schisandra chinensis, Artemisia capillaris, Astragalus membranaceus* or *Poria cocos*. While the highest serum ALT inhibitions were observed when *Myristica* was formulated with *Artemisia*, the lowest inhibition was observed for *Myristica* and *Astragalus* blend.

Moving forward, bearing the optimum efficacy threshold of *Myristica* in mind, the ratio with the lowest percentage inhibition and hence low content of *Myristica* (i.e. MA=*Myristica*:*Astragalus* at 1:4 ratio, respectively) was selected and a third component, such as *Poria* or *Schisandra*, was added to yield compositions designated as MAP and MAS, as earlier outlined. Surprisingly, the addition of *Poria* or *Schisandra* to MA caused a dramatic change in dynamics of inhibitions of serum ALT levels for the given ratios. This time the inhibitions observed were 82.0% and 80.8% for composition MAS (by adding 20% *Schisandra* by weight to the 1:4 ratio of MA and dosage of 400 mg/kg) and composition MAP (by adding 20% *Poria* by weight to the 1:4 ratio of MA and dosage of 400 mg/kg), respectively, in the $CCl_4$ model. When compared to the 41.3% inhibition observed for the MA blend at the 1:4 ratio of the same dosage (400 mg/kg), the current inhibitions observed for MAS (82.0%) and MAP (80.8%) were almost double, and hence signify the importance of the added component of the composition for enhanced liver protections. These findings were also reproduced in the APAP-induced model.

When the merit of formulating these three plant materials (either *Myristica*:*Astragalus*:*Poria* or *Myristica*:*Astragalus*:*Schisandra*) were determined, clearly interesting yet, an unexpected synergy was observed from the combination of these three plant materials that the beneficial effects seen with the MAP or MAS composition treatment exceeded the predicted based on simply summing the effects observed for each of its constituents at the given ratio at the dose of 200 mg/kg.

Collectively, it is understood that combining these traditionally well-known folk medicinal plants into specific ratios to yield MAP or MAS provides a novelty to the composition as demonstrated in its remarkable liver protection activity in multiple animal models.

In contemplated embodiments, the *Myristica* extract and the *Astragalus* extract are blended in a weight ratio ranging from about 4:1 to about 1:4. In other contemplated embodiments, a *Poria* extract is further blended with the MA mixture in a weight percentage of about 5 to about 50%. In contemplated embodiments, the ratio of MAP is about 4:16:5. In yet other embodiments, a *Schizandra* extract is further blended with the MA mixture in a weight percentage of about 5 to about 50%. In contemplated embodiments, the ratio of MAS is about 4:16:5.

Contemplated compounds, medicinal compositions and compositions may comprise or additionally comprise or consist of at least one liver protectant. In some embodiments, the at least one liver protectant may comprise or consist of plant powder or plant extract of milk thistle, curcuma, bupleurum, licorice, salvia, morus, hovenia, agrimony, cudrania, lyceum, citrus, *prunus*, yellow mume, Korea gim, dandelion, *vitis*, grape seed, rubus, camellia, green tea, krill oil, yeast, soy bean; isolated and enriched silymarins, flavonoids, phospholipids, thios, pycnogenols, gelatins, soy lecithin, pancreatic enzymes; natural or synthetic N-acetyl-cysteine, taurine, riboflavin, niacin, pyridoxine, folic acid, carotenes, vitamin A, vitamin B2, B6, B16, vitamin C, vitamin E, glutathione, branched-chain amino acids, selenium, copper, zinc, manganese, coenzyme Q10, L-arginine, L-glutamine, phosphatidylcholine or the like and or a combination thereof.

Also contemplated herein are in vivo metabolic products of the disclosed compounds. Such products may result from, for example, the oxidation, reduction, hydrolysis, amidation, esterification, and the like of the administered compound, primarily due to enzymatic processes. Accordingly, contemplated compounds are those produced by a process comprising administering a contemplated compound or composition to a mammal for a period of time sufficient to yield a metabolic product thereof. Such products are typically identified by administering a radiolabelled compound of this disclosure in a detectable dose to an animal, such as rat, mouse, guinea pig, dog, cat, pig, sheep, horse, monkey, or human, allowing sufficient time for metabolism to occur, and then isolating its conversion products from the urine, blood or other biological samples.

As used herein, the phrases "stable compound" and "stable structure" are used interchangeably and used to indicate a compound that is sufficiently robust to survive isolation to a useful degree of purity from a reaction mixture, and to survive formulation into an efficacious therapeutic agent.

As used herein, the term "mammal" includes humans and both domestic animals, such as laboratory animals or household pets (e.g., rat, mouse, guinea pig, cats, dogs, swine, cattle, sheep, goats, horses, rabbits, primates), and non-domestic animals, such as wildlife or the like.

As used herein, the terms "optional" or "optionally" may be used interchangeably and mean that the subsequently described element, component, event or circumstances may or may not occur, and includes instances where the element, component, event or circumstance occur and instances in which they do not. For example, "optionally substituted aryl" means that the aryl radical may or may not be substituted—in other words, the description includes both substituted aryl radicals and aryl radicals having no substitution.

Contemplated compounds, medicinal compositions and compositions may comprise or additionally comprise or consist of at least one pharmaceutically or nutraceutically acceptable carrier, diluent or excipient. As used herein, the phrase "pharmaceutically or nutraceutically acceptable carrier, diluent or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Contemplated compounds, medicinal compositions and compositions may comprise or additionally comprise or consist of at least one pharmaceutically or nutraceutically acceptable salt. As used herein, the phrase "pharmaceutically or nutraceutically acceptable salt" includes both acid addition and base addition salts.

As used herein, the phrase "pharmaceutically or nutraceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, or the like.

As used herein, the phrase "pharmaceutically or nutraceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include the sodium, potassium, lithium, ammonium, calcium, magnesium, iron, zinc, copper, manganese, aluminum salts and the like. In certain embodiments, the inorganic salts are ammonium, sodium, potassium, calcium, or magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases include isopropylamine, diethylamine, ethanolamine, trimethylamine, dicyclohexylamine, choline, or caffeine.

Often crystallizations produce a solvate of or include contemplated compounds. As used herein, the term "solvate" refers to an aggregate that comprises one or more molecules of a contemplated compound, medicinal composition or composition with one or more molecules of solvent. The solvent may be water, in which case the solvate may be a hydrate. Alternatively, the solvent may be an organic solvent. Thus, the contemplated compounds, medicinal compositions or compositions may exist as a hydrate, including a monohydrate, dihydrate, hemihydrate, sesquihydrate, trihydrate, tetrahydrate and the like, as well as the corresponding solvated forms. A contemplated compound, medicinal composition or composition may be a true solvate, while in other cases, a contemplated compound, medicinal composition or composition may merely retain adventitious water or be a mixture of water plus some adventitious solvent.

A "pharmaceutical composition" or "nutraceutical composition" refers to a formulation of a contemplated compound, medicinal composition or composition and a medium generally accepted in the art for the delivery of the biologically active compound to mammals, e.g., humans. For example, a contemplated pharmaceutical compound, medicinal composition or composition may be formulated or used as a stand-alone composition, or as a component in a prescription drug, an over-the-counter (OTC) medicine, a botanical drug, an herbal medicine, a homeopathic agent, or any other form of health care product reviewed and approved by a government agency. Exemplary and contemplated nutraceutical compositions may be formulated or used as a stand-alone composition, or as a nutritional or bioactive component in food, a novel food, a functional food, a beverage, a bar, a food flavor, a food additive, a medical food, a dietary supplement, or an herbal product. A medium generally accepted in the art includes all pharmaceutically or nutraceutically acceptable carriers, diluents or excipients therefor.

As used herein, the phrase "enriched for" refers to a plant extract or other preparation having at least about a two-fold up to about a 1000-fold increase in the amount or activity of one or more active compounds as compared to the amount or activity of the one or more active compounds found in the weight of the plant material or other source before extraction or other preparation. In certain embodiments, the weight of the plant material or other source before extraction or other preparation may be dry weight, wet weight, or a combination thereof.

As used herein, "major active ingredient" or "major active component" refers to one or more active contemplated compounds found in a plant extract or other preparation, or enriched for in a plant extract or other preparation, which is capable of at least one biological activity. In certain embodiments, a major active ingredient of an enriched extract will be the one or more active compounds that were enriched in that extract. Generally, one or more major active components will impart, directly or indirectly, most (i.e., greater than 50%) of one or more measurable biological activities or effects as compared to other extract components. In certain embodiments, a major active ingredient may be a minor component by weight percentage of an extract (e.g., less than about 50%, 25%, 20%, 15%, 10%, 5%, or 1% of the components contained in an extract) but still provide most of the desired biological activity. Any contemplated composition containing a major active ingredient may also contain minor active ingredients that may or may not contribute to the pharmaceutical or nutraceutical activity of the enriched composition, but not to the level of major active components, and minor active components alone may not be effective in the absence of a major active ingredient.

As used herein, the phrases "effective amount" or "therapeutically effective amount" refer to that amount of a contemplated compound, medicinal composition or composition that, when administered to a mammal, such as a human, is sufficient to effect treatment, including any one or more of: (1) treating or preventing damage of liver cells in a mammal; (2) promoting liver health; (3) preserve detoxification and anti-oxidation liver enzymes in a mammal; (4) increasing liver detoxification capacity in a mammal; (5) treating or preventing liver diseases in a mammal; (6) modifying inflammation of a liver in a mammal; and (7) improving liver renewal function. The amount of a contemplated compound, medicinal composition or composition that constitutes a "therapeutically effective amount" will vary depending on the compound, the condition being treated and its severity, the manner of administration, the duration of treatment, or the body weight and age of a subject to be treated, but can be determined by one of ordinary skill in the art having regard to his own knowledge and to this disclosure.

"Supplements" as used herein refers to a product that improves, promotes, supports, increases, regulates, manages, controls, maintains, optimizes, modifies, reduces, inhibits, or prevents a particular condition, structure or function associated with a natural state or biological process (i.e., are not used to diagnose, treat, mitigate, cure, or prevent disease). In certain embodiments, a supplement is a dietary supplement. For example, with regard to liver health-related conditions, dietary supplements may be used to maintain liver function, minimize liver cell damage, promote healthy liver by protecting antioxidation integrity, diminish the action of free radicals that affect liver health, improve liver detoxification capacity and/or function, support liver function, alleviate liver pain, alleviate liver discomfort, alleviate fatty liver, improve liver detoxification capacity, improve liver immune function, improve liver renewal function or the like. In certain embodiments, dietary supplements are a special category of diet, food or both, and are not a drug.

The terms "treating" or "treatment" or "ameliorating" may be used interchangeably and refer to either a therapeutic treatment or prophylactic/preventative treatment of a disease or condition of interest in a mammal, such as a human, having or suspected of having a disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition, (e.g., relieving pain, reducing inflammation, reducing loss of detoxification capacity) without addressing the underlying disease or condition.

As used herein, the terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. In certain embodiments, contemplated compounds, medicinal compositions, compositions and methods are used to treat, for example, hepatitis, alcohol liver diseases, cirrhosis or both.

As used herein, "statistical significance" refers to a p value of 0.050 or less as calculated using the Students t-test and indicates that it is unlikely that a particular event or result being measured has arisen by chance.

The chemical naming protocol and any structure diagrams used herein are a modified form of the I.U.P.A.C. nomenclature system, using the ACD/Name Version 9.07 software program or ChemDraw Ultra Version 11.0 software naming program (CambridgeSoft), wherein the compounds of this disclosure are named herein as derivatives of the central core structure, e.g., the imidazopyridine structure. For complex chemical names utilized herein, a substituent group is named before the group to which it attaches. For example, cyclopropylethyl comprises an ethyl backbone with cyclopropyl substituent.

In certain embodiments, contemplated compounds and compositions (e.g., pharmaceutical, nutraceutical) may be administered in an amount sufficient to promote liver health; improve liver health; maintain liver health; treat or manage liver health; support liver health; support a normal and comfortable range of liver detox function; improve free radical clearance capacity of liver; reduce the damage of harmful free radicals derived from chemicals, drugs, metabolites, and biological toxins; preserve enzymes that affect liver health, protects from chronic oxidative stress caused liver injury due to Hepatitis B/C virus infection, alcohol consumption, metabolic disorders, non-alcoholic fatty liver disease (NAFLD), non-alcoholic steatohepatitis (NASH), alcoholic liver disease, hepatic encephalopathy, liver fibroproliferative disease (hepatic fibrosis), hepatocyte injury during hypoxia/reoxygenation, or any combination thereof; or any other associated indication described herein, and generally with acceptable toxicity to a patient.

In certain other embodiments, compounds and compositions (e.g., pharmaceutical, nutraceutical) of the present disclosure may be administered in an amount sufficient to treat hepatitis, alcohol liver disease, fatty liver disease, cirrhosis, fibrosis, metabolic syndrome, liver failure, hepatocellular carcinoma, primary biliary cirrhosis, or any other associated indication, and generally with acceptable toxicity to a patient.

Administration of contemplated compounds, medicinal compositions or compositions, or their pharmaceutically or nutraceutically acceptable salts, in pure form or in an appropriate pharmaceutical or nutraceutical composition, can be carried out via any of the accepted modes of administration of agents for serving similar utilities. Contemplated pharmaceutical or nutraceutical compositions can be prepared by combining a contemplated compound with an appropriate pharmaceutically or nutraceutically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. Typical routes of administering such pharmaceutical or nutraceutical compositions include oral, topical, transdermal, inhalation, parenteral, sublingual, buccal, rectal, vaginal, or intranasal.

In some embodiments, a contemplated pharmaceutical or nutraceutical formulation comprises from about 0.5 weight percent to about 90 weight percent of active ingredients of the extract mixture. In some embodiments, contemplated compositions are administered at a dose of about 0.01 to about 500 mg/kg of body weight of the human or animal.

The term "parenteral", as used herein, includes subcutaneous injections, intravenous, intramuscular, intrasternal injection or infusion techniques. Contemplated pharmaceutical or nutraceutical compositions are formulated so as to allow the active ingredients contained therein to be bioavailable upon or soon after administration of the composition to a patient. In some embodiments, contemplated compositions and compounds may be designed or formulated so that they may be time-released after administration.

In certain embodiments, contemplated compositions are administered to a subject or patient in the form of one or more dosage units, where, for example, a tablet may be a single dosage unit, and a container of a contemplated compound in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). A contemplated composition to be administered will, in any event, contain a therapeutically effective amount of a contemplated compound, or a pharmaceutically or nutraceutically acceptable salt thereof, for treatment of a disease or condition of interest in accordance with the teachings of this disclosure.

A contemplated pharmaceutical or nutraceutical composition may be in the form of a solid or liquid. In one aspect, the carrier(s) are particulate, so that the compositions are, for example, in tablet or powder form. The carrier(s) may be liquid, with the compositions being, for example, oral syrup, injectable liquid or an aerosol, which is useful in, for example, inhalatory administration.

When intended for oral administration, the pharmaceutical or nutraceutical composition is in either solid or liquid form, where semi solid, semi liquid, suspension and gel forms are included within the forms considered herein as either solid or liquid.

As a solid composition for oral administration, the pharmaceutical or nutraceutical composition may be formulated into a powder, granule, compressed tablet, pill, capsule, chewing gum, wafer, bar, or like form. Such a solid composition will typically contain one or more inert diluents or edible carriers. In addition, one or more of the following may be present: binders such as carboxymethylcellulose, ethyl cellulose, cyclodextrin, microcrystalline cellulose, gum tragacanth or gelatin; excipients such as starch, lactose or dextrins, disintegrating agents such as alginic acid, sodium alginate, Primojel®, corn starch and the like; lubricants such as magnesium stearate or Sterotex®; glidants such as colloidal silicon dioxide; sweetening agents such as sucrose or saccharin; a flavoring agent such as peppermint, methyl salicylate or orange flavoring; and a coloring agent.

When the pharmaceutical or nutraceutical composition is in the form of a capsule, for example, a gelatin capsule, it may contain, in addition to materials of the above type, a liquid carrier such as polyethylene glycol or oil.

A contemplated pharmaceutical or nutraceutical composition may be in the form of a liquid, for example, an elixir, syrup, gel, solution, emulsion or suspension. The liquid may be for oral administration or for delivery by injection, as two examples. When intended for oral administration, a useful composition contains, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A contemplated liquid pharmaceutical or nutraceutical compositions, whether they be solutions, suspensions or other like form, may include one or more of the following adjuvants: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a generally useful adjuvant. An injectable pharmaceutical or nutraceutical composition is sterile.

A contemplated liquid pharmaceutical or nutraceutical composition intended for either parenteral or oral administration should contain an amount of a contemplated compound, medicinal composition or composition such that a suitable dosage will be obtained.

A contemplated pharmaceutical or nutraceutical composition may be intended for topical administration, in which case the carrier may suitably comprise a solution, emulsion, cream, lotion, ointment, or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical or nutraceutical composition for topical administration. If intended for transdermal administration, the composition may include a transdermal patch or iontophoresis device.

A contemplated pharmaceutical or nutraceutical composition may be intended for rectal administration, in the form, for example, of a suppository, which will melt in the rectum and release the drug. The composition for rectal administration may contain an oleaginous base as a suitable nonirritating excipient. Such bases include lanolin, cocoa butter and polyethylene glycol.

A contemplated pharmaceutical or nutraceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

A contemplated pharmaceutical or nutraceutical composition in solid or liquid form may include an agent that binds to the contemplated compound and thereby assists in the delivery of the compound. Suitable agents that may act in this capacity include a monoclonal or polyclonal antibody, a protein or a liposome.

A contemplated pharmaceutical or nutraceutical composition in solid or liquid form may include reducing the size of a particle to, for example, improve bioavailability. The size of a powder, granule, particle, microsphere, or the like in a composition, with or without an excipient, can be macro (e.g., visible to the eye or at least 100 μm in size), micro (e.g., may range from about 100 μm to about 100 nm in size), nano (e.g., may no more than 100 nm in size), and any size in between or any combination thereof to improve size and bulk density.

A contemplated pharmaceutical or nutraceutical composition may comprise or consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi phasic, or tri phasic systems in order to deliver the active ingredient(s). Delivery of the aerosol includes the necessary container, activators, valves, subcontainers, and the like, which together may form a kit. One skilled in the art, without undue experimentation, may determine the most appropriate aerosol(s).

A contemplated pharmaceutical or nutraceutical composition may be prepared by methodology well known in the pharmaceutical or nutraceutical art. For example, a pharmaceutical or nutraceutical composition intended to be administered by injection can be prepared by combining a contemplated compound with sterile, distilled water so as to form a solution. A surfactant may be added to facilitate the formation of a homogeneous solution or suspension. Surfactants are compounds that non-covalently interact with a contemplated compound so as to facilitate dissolution or homogeneous suspension of the compound in the aqueous delivery system.

Contemplated compounds, compositions and medicinal compositions, or their pharmaceutically or nutraceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Contemplated compounds, compositions and medicinal compositions, or pharmaceutically or nutraceutically acceptable derivatives thereof, may also be administered simultaneously with, prior to, or after administration of one or more other therapeutic agents. Such combination therapy includes administration of a single pharmaceutical or nutraceutical dosage formulation that contains a contemplated compound and one or more additional active agents, as well as administration of a contemplated compound and each active agent in its own separate pharmaceutical or nutraceutical dosage formulation. For example, a contemplated compound and another active agent can be administered to the patient together in a single oral dosage composition, such as a tablet or capsule, or each agent can be administered in separate oral dosage formulations. Where separate dosage formulations are used, contemplated compounds and one or more additional active agents can be administered at essentially the same time, i.e., concurrently, or at separate staggered times, i.e., sequentially; combination therapy is understood to include all these regimens.

It is understood that in the present description, combinations of substituents or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include C(O)R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley, which is incorporated by reference herein in its entirety. As one of skill in the art would appreciate, a protecting group may also be a polymer resin such as a Wang resin, Rink resin or a 2-chlorotrityl-chloride resin.

It will also be appreciated by those skilled in the art, although such protected derivatives of contemplated compounds may not possess pharmacological activity as such, they may be administered to a mammal and thereafter metabolized in the body to form compounds which are pharmacologically active. Such derivatives may therefore be described as "prodrugs". All prodrugs of contemplated compounds are included within the scope of this disclosure.

Furthermore, contemplated compounds that exist in free base or acid form can be converted to their pharmaceutically or nutraceutically acceptable salts by treatment with the appropriate inorganic or organic base or acid by methods known to one skilled in the art. Salts of contemplated compounds can be converted to their free base or acid form by standard techniques.

In some embodiments, contemplated compounds, compositions and/or medicinal compositions can be isolated from plant sources, for example, from those plants included in the Examples and elsewhere throughout the present application. Suitable plant parts for isolation of contemplated extracts and compounds include leaves, bark, trunk, trunk bark, stems, stem bark, twigs, tubers, root, root bark, bark surface (such as periderm or polyderm, which may include phellem, phellogen, phelloderm, or any combination thereof), young shoots, rhizomes, seed, fruit, androecium, gynoecium, calyx, stamen, petal, sepal, carpel (pistil), flower, or any combination thereof. Contemplated plant extracts are derived from at least one plant part selected from the group consisting of stems, stem barks, trunks, trunk barks, twigs, tubers, roots, root barks, young shoots, seeds, rhizomes, flowers and other reproductive organs, leaves, other aerial parts or a combination thereof. In some related embodiments, contemplated compounds are isolated from plant sources and synthetically modified to contain any of the recited substituents. In this regard, synthetic modification of contemplated compounds isolated from plants can be accomplished using any number of techniques that are known in the art and are well within the knowledge of one of ordinary skill in the art.

EXAMPLES

Example 1: Animals

Purpose bred mice at the age of 7-8 weeks with body weight of 25-30 g were purchased form Charles River Laboratories (Wilmington, Mass.). Animals were acclimated upon arrival for a week before being weighed and assigned randomly to their respective groups. ICR mice (5/cage) were housed in a polypropylene cage and individually identified by numbers on their tail. Each cage was covered with wire bar lid and filtered top (Allentown, N.J.). Each individual cage was identified with a cage card indicating project number, test article, dose level, group, and an animal number. The Harlan T7087 soft cob bedding was used and changed at least twice weekly. Animals were provided with fresh water and rodent chow diet #T2018 (Harlan Teklad, 370W, Kent, Wash.) ad libitum and were housed in a temperature controlled room (22.2° C.) on a 12 hour light-dark cycle. All animal experiments were conducted according to institutional guidelines congruent with guide for the care and use of laboratory animals.

Example 2: Acetaminophen (APAP) or Carbon Tetrachloride (CCL4)-Induced Liver Damage Animal Models A balanced therapeutic schedule was generated and optimized as follows to address prophylaxis and intervention: for APAP-induced hepatotoxicity model, APAP (Lot #MKBQ8028V, from Sigma) at a dose of 400 mg/kg dissolved in warm saline (Lot #132908 from G-Biosciences, Lot #720729 from Quality Biological) (heated to 60° C. and cooled down to ambient temperature) was orally administered to overnight fasted ICR/CD-1 mice to induce toxicity. For the $CCl_4$-induced hepatotoxicity model, $CCl_4$ (Lot #SHBD5351V, from Sigma) at a dose of 25 μl/kg dissolved in corn oil was administered intraperitoneally to overnight fasted ICR/CD-1 mice to induce toxicity. For both models, materials were administered at −48 hr, −24 hr, −2 hr before APAP or $CCl_4$ administrations and +6 hr after induction. In total, the mice received 3 doses before the chemical induction and a dose after the chemical induction. 10% Tween-20 (Lot #0134C141 from Amresco), 1% CMC (Lot #NH0454 from Spectra) or 1% MC (Lot #5LBK4357V) were used as a carrier vehicle for all the materials. Control mice without APAP or $CCl_4$ received carrier vehicle only. Serum ALT was determined at T24 (Phoenix Laboratories, Everett, Wash.).

Example 3: Preparation of Organic Extracts and Screening for Liver Protection Efficacy Plants were collected and prepared with different solvents based on their active compounds properties and screened in our hepatotoxicity animal models in mice. The following plants in Table 1 showed serum ALT inhibition at different levels either in acetaminophen-induced model or $CCl_4$ induced model in mice. Only plants with efficacies in both models will be selected for further studies.

TABLE 1

Summary of plant extracts

| Plant Name | Code | Plant Parts | Extraction Method | Specification |
|---|---|---|---|---|
| Ganoderma lucidum | L0494 | mushroom | ethanol extracts | NLT 13.5% polysaccharides and 6% triterpenoids |
| Pueraria lobata | L0500 | roots | ethanol extracts | 40% isoflavones |
| Poria cocos | L0501 | fungus | Water/ethanol extracts | NLT 20% polysaccharides NLT 10% triterpenoids |
| Astragalus membranaceus | L0497 | roots | Water extracts | NLT 10% polysacharides, NLT 0.3% astragaloside |
| Myristica fragrans | R603-70E | seeds | 70% Ethanol extract | — |
| Schisandra chinensis | L0499 | seeds | Ethanol extracts | NLT 8% schisandins |
| Schisandra chinensis | L0498 | fruits | Ethanol extracts | NLT 2% schisandins |
| Artemisia capillaris | R0594 | aerial parts | 70% Ethanol extract | NLT 3% chlorogenic acid |

Example 4: Liver Protection Activity of Plant Extracts on APAP and CCL4-Induced Hepatotoxicity Model Plant materials from legacy mining collected based on their historical usage on liver protection and renewal were extracted using 70% ethanol and screened for their efficacy in both APAP and $CCl_4$-induced liver toxicity. Materials were administered to animals orally at a dosage specified in Table 2. As depicted in the table below, various degrees of inhibition in serum ALT and significance were observed when mice were treated with the extracts at the disclosed dosages. The highest inhibition, 94.4% in the APAP model and 47.6% in the $CCl_4$ model were observed for extracts *Myristica* fragrance and *Schisandra chinensis*, respectively.

TABLE 2

Percent inhibition of serum ALT for plant extracts in APAP/$CCl_4$-induced liver toxicity model

| N | Material | Code | Part | APAP (400 mg/kg) Dose (mg/kg) | % Change | P-values | CCl4 (25 μl/kg) Dose (mg/kg) | % Change | P-values |
|---|---|---|---|---|---|---|---|---|---|
| 5 | Control (—) | — | — | 0 | — | — | 0 | — | — |
| 10 | APAP/CCL4 | — | — | 400 | — | — | 25 | — | — |
| 10 | *Ganoderma lucidem* | L494 | Mushroom | 400 | 21.5 | 0.54 | 500 | 25.1 | 0.05 |
| 10 | *Astragalus membranaceus* | L497 | Roots | 400 | 50.9 | 0.12 | 500 | 34.1 | 0.02 |
| 10 | *Pueraria lobata* | L500 | Roots | 400 | 2.1 | 0.95 | 500 | 25.0 | 0.045 |
| 10 | *Poria cocos* | L501 | Fungus | 400 | 41.0 | 0.21 | 500 | 38.1 | 0.01 |
| 10 | *Myristica fragrance* | R603 | seed | 400 | 94.4 | 0.001 | 500 | 37.6 | 0.25 |
| 10 | *Schisandra chinensis* | L498/L499 | Fruit/Seeds | 400 | 41.4 | 0.04 | 500 | 47.6 | 0.001 |
| 10 | *Artemisia capillaries* | R594/R684 | Whole plant | 500 | 47.0 | 0.02 | 400 | 42.7 | 0.01 |

While very similar level of inhibitions were observed in both models for the rest of the extracts, among the compiled plant materials, efficacies for *Pueraria lobata* and *Ganoderma lucidem* were mainly limited to the $CCl_4$ model and failed to show reproducibility either in percentage or significance in APAP model. In particular, regardless of significance, extracts with greater or equal to 30% inhibitions in either of the models were subjected to further evaluations.

Example 5: Preparation of *Astraqalus Membranaceus* and *Poris Cocos* Extracts Ground *Astragalus membranaceus* root powder could be extracted with water to get water extract with specification of no less than 20% polysaccharides by UV colorimetric method and no less than 0.3% astragaloside by HPLC method. Similar results were obtained with the solvent being replaced with methanol or ethanol to provide a methanol extract (ME) or ethanol extract (EE), ethanol:$H_2O$ (7:3) extracts, ethanol:$H_2O$ (1:1) extracts, and ethanol:$H_2O$ (3:7) extracts respectively.

Dried and ground fruit body of Poris *cocos* were extract with ethanol first, then water to extract both non-polar components and polar components. The ethanol extract and water extracts were combined together to give the final *Poris cocos* extracts with specification of no less than 20% polysaccharides by UV colorimetric method and no less than 10% triterpenes by HPLC or by colorimetric method. Similar results were obtained with the solvent being replaced with methanol or ethanol to provide a methanol extract (ME) or ethanol extract (EE), ethanol:$H_2O$ (7:3) extracts, ethanol:$H_2O$ (1:1) extracts, ethanol:$H_2O$ (3:7) extracts and water extracts respectively.

Example 6: Preparation of Organic Extracts of *Artemisia Capillaris*

Dried ground aerial parts *Artemisia capillaris* (2.5 kg) were cut, crushed, and then extracted with approximately 15-fold volume (37.5 L) of 70% ethyl alcohol in water (v/v). The extraction was carried out at 85° C. for 3 hrs. After filtration, the ethanol solution was concentrated by rotatory evaporator under vacuum at 40° C. This extraction and concentration procedure was repeated two times with 10 fold volume (25 L) of 70% ethyl alcohol in water (v/v) for 2 hrs. The concentrated extract solution was evaporated to dryness by vacuum dry oven to give 480 g of *Artemisia capillaris* 70% EtOH extract powder (lot #RN367-3-60M) with extraction yield 19.2%.

Dried ground *Artemisia capillaris* herb (180.4) g was extracted with 70% ethanol in water three times by refluxing one hour each time. The organic solution was combined and evaporated under vacuum to provide 70% ethanol extract (R594-70EE) 37.7 g with a yield of 20.9%. Similar results were obtained using the same procedure, but with the organic solvent being replaced with methanol or ethanol to provide a methanol extract (ME) or ethanol extract (EE), ethanol:$H_2O$ (7:3) extracts, ethanol:$H_2O$ (1:1) extracts, ethanol:$H_2O$ (3:7) extracts and water extracts respectively.

Example 7: Preparation of Organic Extracts from *Schisandra Chinensis* Fruit A total of 20 g of dried fruit of *Schisandra chinensis* were loaded into two 100 ml stainless steel tube and extracted twice with an organic 70% EtOH in water using an ASE 300 automatic extractor at 80 degree and pressure 1500 psi. The extract solution was automatically filtered and collected. The combined solution was evaporated to dryness by rotary evaporator to give crude 70% EtOH extract (9.65 g, 49.5%).

Similar results were obtained using the same procedure, but with the organic solvent being replaced with methanol or ethanol to provide a methanol extract (ME) or ethanol extract (EE), ethanol:$H_2O$ (7:3) extracts, ethanol:$H_2O$ (1:1) extracts, ethanol:$H_2O$ (3:7) extracts and water extracts respectively.

Schisandra chinensis extracts were manufactured with extraction of dried fruit by 70% ethanol/30% water (v/v). The extract was further processed to give extract in power form (Lot #) with no less than 2% total Schisandrins, including schisandrin, schisantherin A, schisandrin A (deoxyschisandrin), and schisandrin B.

Example 8: HPLC Analysis and Quantification of Schisandra Chinensis Extracts

Schisandra chinensis fruits were extracted with water. After filtration, the water solution were further concentrated to dryness by spray drying. The fruit nuts were dried and ground to powder and extracted with ethanol. The ethanol solution were filtered, concentrated and further dried out by spray drying after mixing with maltodextrin. The water extract and ethanol extract were blended together to make the final Schisandra chinensis extracts with 7.1% total Schisandrins, including schisandrin, schisantherin A, schisandrin A (deoxyschisandrin), and schisandrin B.

Four active marker compounds, schisandrin (lot #110857, National institute for food and control, china), schisantherin A (lot #11529-200503, National institute for food and control, china), schisandrin A (deoxyschisandrin, lot #110764-200107, National institute for food and control, china), and schisandrin B (lot #110765-200508, National institute for food and control, china) were identified in Schisandra chinensis extracts and confirmed with Schisandra chinensis reference standard material (lot #140217, National Institute for Food and Control, China).

Active marker compounds were quantified by HPLC using a C18 reversed-phase column (Phenomenex, Luna C18, 10 μm, 250 mm×4.6 mm) in a Hitachi HPLC system with UV wavelength 250 nm by comparing to the reference standard material. The column was eluted with water and acetonitrile at 1 mL/min flow rate. A gradient table for this Example is shown in Table 3. Each individual peak was identified and integrated, and then total content of four compounds including schisandrins, schisantherin A, schisandrin A and schisandrin B were calculated based on RSM and that information is shown in Table 4. Total schisandrins in schisandra fruit extracts could be found in a range of 1-8%.

TABLE 3

HPLC mobile phase gradient table for Schisandra chinensis extracts quantification

| Time (min) | H$_2$O (%) | MeOH (%) |
|---|---|---|
| 0 | 35 | 65 |
| 20 | 32 | 68 |
| 21 | 25 | 75 |
| 36 | 25 | 75 |
| 37 | 35 | 65 |
| 45 | 35 | 65 |

TABLE 4

Schisandins content in Schisandra chinensis extracts

| Sample code | Schisandrin | schisantherin A | deoxyschisandrin | schisandrin B | total schisandrins |
|---|---|---|---|---|---|
| L531 | 0.03% | 0.87% | 0.07% | 0.04% | 1.01% |
| L0498 | 1.16% | 0.10% | 0.23% | 0.58% | 2.07% |
| L499 | 3.80% | 0.69% | 0.77% | 1.84% | 7.10% |

Example 9: HPLC Quantification of Organic Acids in Schisandra Fruit Extracts

The presence of malic acid, shikimic acid and citric acid in 70% EtOH extracts generated in-house from different collections have been confirmed and are set forth in the Table 5. The organic acids were quantitatively analyzed by HPLC using a Hypersil GOLD aQ column (4.6×250 mm, 5 μm), and under isocratic conditions for 20 minutes at 5° C. with 50 mM potassium dihydrogen phosphate (adjusted pH to 2.8 with H$_3$PO$_4$) as the mobile phase, and with the flow rate at 0.7 ml/min. The organic acids were detected using a UV detector at 205 nm and identified based on retention time by comparison with organic acids standards.

TABLE 5

HPLC quantification of Organic Acids Content in Extracts of Schisandra chinensis

| Extracts | % Malic acid | % Shikimic acid | % Citric acid | Total % Organic acid |
|---|---|---|---|---|
| R768-70E-Fruit | 8.2% | 3.2% | 22.5% | 33.8% |
| R685-70E-Fruit | 15.5% | 2.9% | 26.5% | 44.9% |
| R767-70E-Fruit | 10.6% | 3.5% | 32.4% | 46.5% |
| R597-70E-Fruit | 14.4% | 3.3% | 18.8% | 36.6% |
| R768-70E-Meat | 9.1% | 2.4% | 20.6% | 32.2% |
| R768-70E-Seed | 4.9% | 1.3% | 8.5% | 14.7% |
| R685-70E-Seed | 7.7% | 1.3% | 10.8% | 19.9% |
| R766-70E-Seed | 0.8% | 0.0% | 1.3% | 2.1% |
| L498 | 0.1% | 0.8% | 0.0% | 0.8% |
| L499 | 0.3% | 0.5% | 0.0% | 0.8% |
| E1467 | 0.0% | 0.1% | 0.0% | 0.1% |
| E1469 | 0.0% | 0.2% | 0.0% | 0.2% |
| L529 | 0.0% | 0.2% | 0.0% | 0.2% |

Example 10: Preparation of Myristica Fragrans Extracts

Dried ground Myristica fragrans seeds (304 g) were extracted with 70% ethanol in water three times by refluxing one hour each time. The organic solution was combined and evaporated under vacuum to provide 70% ethanol extract (R603-70E) 46.3 g with a yield of 15.2%. Similar results were obtained using the same procedure, but with the organic solvent being replaced with methanol or ethanol to provide a methanol extract (ME) or ethanol extract (EE), ethanol:H$_2$O (7:3) extracts, ethanol:H$_2$O (1:1) extracts, ethanol:H$_2$O (3:7) extracts and water extracts respectively.

Example 11: HPLC Analysis and Quantification of Myristica Fragrans Extracts

Myristicin was the maceligan compound reported from *Myristica fragrans* with hepatoprotective property. *Myristica fragrans* extracts were analyzed by quantifying myristicin (15201, Cayman, USA) by HPLC with a C18 reversed-phase column (Phenomenex, Luna C18, 10 µm, 250 mm×4.6 mm) in a Hitachi HPLC system. The column was eluted with a gradient elution with 40% MeOH in water to 100% MeOH in 18 min at a flow rate of 1 mL/min with UV wavelength at 250 nm. *Myristica fragrans* seed extracts were dissolved in MeOH with a concentration of 10 mg/mL and analyzed by injection of 20 uL solution. Myristicin content in 70% ethanol extracts ranged from 2% to 6%. No decent myristicin peak could be detected in water extract (L530-WE). The 70% ethanol extracts and water extracts were tested in $CCl_4$ induced liver toxicity mice model. Both Water extract and 70% ethanol extracts showed hetatoprotective activity at 400 mg/kg, with 32.63% inhibition for water extracts, 95.61% inhibition for 70% ethanol extracts. Table 6 shows Myristicin content in *Myristica fragrans* extract and in vivo data.

TABLE 6

Myristicin content in *Myristica fragrans* extract and in vivo data

| Sample name | Myristicin content | Dose (mg/kg) | ALT % change | p value |
|---|---|---|---|---|
| L530-WE | ND | 400 | 32.63 | 0.060 |
| L532-70E | 2.07% | 400 | 95.61 | 0.000 |
| R603-70E | 5.92% | 200 | 99.50 | 0.000 |

*ND—not detected

Example 12: Fractionation of Myristica Fragrans Extracts

The *Myristica fragrans* 70% ethanol extract (R603-70E, 10 g) was partitioned between hexanes (100 mL) and water (150 mL) for three times. The combined hexanes solution was freed from solvent by vacuum to give hexanes extract (HE) 5.6 g. The aqueous layer was extracted with ethyl acetate (100 mL) for three times. The combined ethyl acetate layers were dried out in vacuum to give the ethyl acetate extract (EA) 1.3 g. The aqueous layer was further extracted with butanol (100 mL) for three times to give butanol extract (BU) 0.7 g. The remaining aqueous layer was freeze-dried to give aqueous extract (WA) 2.3 g. HE, EA, BU and WA were further analyzed by HPLC and tested in $CCl_4$ induced hepatotoxicity model in mice.

Myristicin was mainly found in HE, not detected in EA, BU and WA. Myristicin (15201, Cayman, USA) was tested in the same model and showed potent efficacy with 99.7% ALT inhibition at 50 mg/kg. HE, containing as high as 27.5% myristicin, showed similar inhibition with 95.3% ALT level reduction at 200 mg/kg level with P≤0.01 compared to myristicina at 50 mg/kg dosage, indicating Myristicin is one of the main active compound responsible for the hepatoprotecive efficacy of the crude extracts. EA, BU and WA were found inactive in this $CCl_4$ model at the same dosage 200 mg/kg. Table 7 shows the Myristicin content and in vivo efficacy of *Myristica fragrans* partition fractions.

TABLE 7

Myristicin content and in vivo efficacy of *Myristica fragrans* partition fractions

| Sample name | weight ratio | Myristicin content | Dose (mg/kg) | ALT % change | p value |
|---|---|---|---|---|---|
| R00603-HE | 56.05% | 27.51% | 200 | 95.32 | 0.000 |
| R00603-EA | 13.14% | ND | 200 | −41.98 | 0.020 |
| R00603-BU | 7.84% | ND | 200 | −0.11 | 0.995 |
| R00603-WA | 23.41% | ND | 200 | −1.81 | 0.920 |

*ND—not detected

Example 13: Dose-Response Effect of Myristica Fragrans Extracts and Their Fractions in $CCl_4$-Induced Hepatotoxicity Model $CCl_4$-induced hepatotoxicity model was utilized to evaluate the dose-correlated liver protection activity of *Myristica* fragrance and its fractions. While each fraction was tested at a dose of 200 mg/kg, dose ranges of 50-200 mg/kg were selected for the dose-response study. In this study, a possible active marker, Myristicin, at a dose of 50 mg/kg was also tested. As seen in Table 8 below, a clear dose—correlated inhibition was observed for the mice treated with 50-200 mg/kg of *Myristica* (i.e. 44.8-99.5% inhibitions). Almost a complete inhibition in liver injury caused by carbon tetrachloride was observed when mice were treated with *Myristica* at a dose of 200 mg/kg. These data suggest that for a 50% inhibition in serum ALT to occur, mice may need to be treated with *Myristica* at a dose level between 50-75 mg/kg.

While butanol, ethanol and water extract fractions were inactive in this model, mice treated with the hexane extract portion showed 95.3% inhibitions in serum ALT when compared to vehicle treated injured mice.

TABLE 8

Dose-correlated liver protection effect of *Myristica fragrans* and its fractions in CCL4-induced hepatotoxicity model

| Material | Solvent | Dose (mg/kg) | N | CCL4 (µl/kg) | % Change | P-values |
|---|---|---|---|---|---|---|
| Control (—) | | 0 | 5 | 0 | — | — |
| CCL4 | | 0 | 10 | 25 | — | — |
| Myristica fragrance (R603) | EE | 50 | 10 | 25 | 44.8 | 0.0031 |
| | | 100 | 10 | 25 | 92.6 | 0.0000 |
| | | 200 | 10 | 25 | 99.5 | 0.0000 |
| R603 | HE | 200 | 10 | 25 | 95.3 | 0.0000 |
| | EA | 200 | 10 | 25 | −42.0 | 0.0170 |
| | BU | 200 | 10 | 25 | −0.1 | 0.9948 |
| | WA | 200 | 10 | 25 | −1.8 | 0.9167 |
| Myristicin | — | 50 | 10 | 25 | 99.7 | 0.0000 |

Mice treated with 50 mg/kg of Myristicin exhibited 99.7% inhibitions in serum ALT when compared to vehicle treated injured mice confirming the possibility Myristicin as a major active compound in the *Myristica* fragrance.

Example 14: Liver Protection Activity of Myristica Fragrans Extracts with Schisandra Chinensis, Artemisia Capillaris, Astraqalus Membranaceus or Poria Cocos in $CCl_4$-Induced Hepatotoxicity Model Documenting individual liver protection data for lead plants, a search for unexpected or enhanced outcome using unpredicted blending for these plant materials was started by formulating them in specific ratios such as 1:1, 1:2, 2:1, 1:4 and 4:1. Due to its highest degree of inhibition, *Myristica* fragrance was selected as a major component to pair with each plant material for the indicated ratios in CCL4 model and tested at a dose of 400 mg/kg. As seen in the Table 9 below, statistically significant inhibitions in serum ALT and hence presumed liver protection from carbon tetrachloride induced injury were observed for all the ratios when *Myristica* fragrance was formulated with *Schisandra chinensis, Artemisia capillaris, Astragalus membranaceus* or *Poria cocos*. The ranges of inhibitions were, 42.4-70.0%, 41.3-80.7%, 88.8-99.8% and 91.0-99.8% when *Myristica* was blended with *Schisandra, Astragalus, Artemisia* and *Poria*, respectively. The highest liver protection activities were observed when *Myristica* was blended with *Artemisia* (2:1 and 4:1) and *poria* (1:1); the lowest liver protection activity was observed when *Myristica* was formulated with *Astragalus* at a 1:1 ratio.

composition of *Myristica* and *Astragalus* at a 1:4 ratios, respectively. As depicted in Table 10 below, in fact the addition of *Schisandra* or *Poria* caused a dramatic change in dynamics of inhibitions of serum ALT levels for the given ratios. This time the inhibitions observed were 82.0% and 80.8% for composition MAS2 (by adding 20% *Schisandra*) and composition MAP2 (by adding 20% *Poria*), respectively, in the CCL4 model. When compared to the 41.3% inhibition observed for the blend *Myristica* and *Astragalus* (MA) alone at the 1:4 ratio, the current inhibitions observed for MAS2 and MAP2 were almost double and hence signify the importance of the added component of the composition for enhanced liver protections. On the other hand, regardless of the percentage of *Schisandra* added to the composition MA to yield MAS (either 10% or 20%), more than 90% inhibitions in serum ALT were observed in the APAP

TABLE 9

Efficacy of compositions of *Myristica* blended with *Schisandra, Astragalus, Artemisia* or *Poria* in CCL4-induced hepatotoxicity model

| Material | Ratio | N | Dose (400 mg/kg) | CCL4 (µl/kg) | % Change | P-values |
| --- | --- | --- | --- | --- | --- | --- |
| Control (—) | 0 | 5 | 0 | 0 | — | — |
| CCL4 | 0 | 10 | 0 | 25 | — | — |
| *Myristica:Schisandra* | 1:1 | 10 | 200:200 | 25 | 61.1 | 0.0000 |
|  | 1:2 | 10 | 133.3:266.7 | 25 | 46.2 | 0.0001 |
|  | 2:1 | 10 | 266.7:133.3 | 25 | 52.3 | 0.0000 |
|  | 1:4 | 10 | 80:320 | 25 | 42.4 | 0.0018 |
|  | 4:1 | 10 | 320:80 | 25 | 70.0 | 0.0000 |
| *Myristica:Astragalus* | 1:1 | 10 | 200:200 | 25 | 48.8 | 0.0017 |
|  | 1:2 | 10 | 133.3:266.7 | 25 | 53.2 | 0.0001 |
|  | 2:1 | 10 | 266.7:133.3 | 25 | 80.7 | 0.0000 |
|  | 1:4 | 10 | 80:320 | 25 | 41.3 | 0.0003 |
|  | 4:1 | 10 | 320:80 | 25 | 68.1 | 0.0000 |
| *Myristica:Artemisia* | 1:1 | 10 | 200:200 | 25 | 99.7 | 0.0000 |
|  | 1:2 | 10 | 133.3:266.7 | 25 | 97.2 | 0.0000 |
|  | 2:1 | 10 | 266.7:133.3 | 25 | 99.8 | 0.0000 |
|  | 1:4 | 10 | 80:320 | 25 | 88.8 | 0.0001 |
|  | 4:1 | 10 | 320:80 | 25 | 99.8 | 0.0000 |
| *Myristica:Poria* | 1:1 | 10 | 200:200 | 25 | 99.8 | 0.0000 |
|  | 1:2 | 10 | 133.3:266.7 | 25 | 96.5 | 0.0000 |
|  | 2:1 | 10 | 266.7:133.3 | 25 | 99.7 | 0.0000 |
|  | 1:4 | 10 | 80:320 | 25 | 91.0 | 0.0001 |
|  | 4:1 | 10 | 320:80 | 25 | 99.4 | 0.0000 |

Example 15: Evaluation of Liver Protection Activity of *Myristica Fragrans* Extracts with *Schisandra Chinensis, Artemisia Capillaris, Astraqalus Membranaceus* or *Poria Cocos* at Specific Ratios in CCl$_4$-Induced Hepatotoxicity Model Given the fact that the 1:4 ratio of *Myristica* formulated with *Astragalus* resulted in the lowest inhibition in serum ALT (i.e. 41.3%), a third component (either *Schisandra* or *Poria*) was selected to be added at a 10% or 20% by weight to the total dose of 400 mg/kg and assessed for a change in response in liver protection activity both in the CCL4 and APAP induced hepatotoxicity models. "MA" stands for a induced hepatotoxicity model. These greater inhibitions were also shared when *Poria* was added at 20% by weight to MA to yield MAP i.e. 92.7% in the APAP model.

These collective data suggest that unpredicted enhanced liver protection activities could be achieved while multiple compositions showed efficacy in protecting the liver, the highest protection were observed when 20% of *Poria cocos* or *Schizandra chinensis* extracts by weight was added in a 1M:4A ratio in both models yielding a final 4m:16A:5p or 4m:16A:5s ratio for the composition MAP or MAS. As a result, this ratio, 4:16:5 ratio considered as the lead composition. By combining three historically well-known plants at specific ratios indicated above.

TABLE 10

Efficacy of composition MAP or MAS in APAP/CCL4-induced hepatotoxicity model

| Material | Ratio | R603/L497/L501 or L498 | Dose (mg/kg) | APAP (N = 11) | | CCL4 (N = 9) | | |
|---|---|---|---|---|---|---|---|---|
| | | | Dose (mg/kg) | % Change | P-values | Dose (mg/kg) | % Change | P-values |
| Control (—) | — | 0 | 0 | — | — | 0 | — | — |
| APAP/CCL4 | — | 0 | 400 | — | — | 25 | — | — |
| Composition MAP1 | (1:4) 10% | 72/288/40 | 400 | 68.4 | 0.0564 | 25 | 74.4 | 0.0025 |
| Composition MAP2 | (1:4) 20% | 64/256/80 | 400 | 92.7 | 0.0073 | 25 | 80.8 | 0.0007 |
| Composition MAS1 | (1:4) 10% | 72/288/40 | 400 | 91.5 | 0.0080 | 25 | 70.8 | 0.0020 |
| Composition MAS2 | (1:4) 20% | 64/256/80 | 400 | 91.2 | 0.0112 | 25 | 82.0 | 0.0006 |

MAP = *Myristica:Astragalus:Poria*
MAS = *Myristica:Astragalus:Schisandra*
R603 = *Myristica*
L497 = *Astragalus*
L501 = *Poria*
L498 = *Schisandra*

Example 16: Dose-Response Effect of Composition Comprising *Myristica Fragrans* Extracts with *Schisandra Chinensis*, *Astragalus Membranaceus* and/or *Poria Cocos* at Specific Ratios in APAP and CCl$_4$-Induced Hepatotoxicity Model Once the excelled liver protection capacity of the compositions MAP and MAS was documented by adding a third component at 20% by weight to the 1:4 ratio of *Myristica* and *Astragalus*, the optimum dosages of these compositions that would incur significant liver protection were evaluated both in APAP and CCL4 induced models. Mice were gavaged orally the compositions MAP and MAS at doses of 200 mg/kg, 300 mg/kg and 400 mg/kg suspended in 10% tween 20. The vehicle control group received the carrier solution only. As seen in Table 11, in the CCL4-induced toxicity model, dose-correlated inhibitions in serum ALT were observed for the compositions. 66.9% (p=0.0015), 80.0% (p=0.0002) and 83.7% (p=0.0002) inhibitions for MAP, 54.1% (p=0.0109), 74.9% (p=0.0004) and 79.7% (p=0.0002) inhibitions for MAS were observed for mice treated with doses of 200 mg/kg, 300 mg/kg and 400 mg/kg, respectively. Similarly, in the APAP-induced injury model, dose-correlated inhibitions in serum ALT were observed for the compositions. 25.8% (p=0.49), 62.9% (p=0.01) and 88.1% (p=0.0001) inhibitions for MAP, 32.4% (p=0.16), 62.7% (p=0.02) and 78.7% (p=0.0007) inhibitions for MAS were observed for mice treated with doses of 200 mg/kg, 300 mg/kg and 400 mg/kg, respectively. Even though the inhibitions observed at the 200 mg/kg dosage was not statistically significant in the APAP model for both the compositions, the inhibitions in serum ALT observed were far greater than the individual components of the compositions suggesting the clear advantage of formulating these three individual materials to yield the compositions MAP and MAS for a better liver protection activity. While there was a 100% survival rate for all the groups in the CCL4 model, this rate ranges from 50-100% for MAP and 70-700% for MAS in the APAP model. In parallel with the efficacy, the survival rates observed in the APAP model were correlated to the amount of the compositions administered to the animals. For instance, while mice received 200 mg/kg of MAP or MAS had 50% and 70% survival rates, respectively, a 100% survival rate was observed for both the compositions at the highest dose administered (400m g/kg).

Here we tested the efficacy of individual plants such as *Myristica*, *Astragalus*, *Schisandra*, and *Poria* at a dosage equivalent to each plant ratio in the compassions MAP and MAS as they appear in the lowest dose tested (200 mg/kg). As seen in the Table 11, in the CCL4 model *Myristica* at the dose of 32 mg/kg resulted in 40.7% inhibitions in serum ALT with a 100% survival rate in the CCL4 model. The rest of the components of the compositions aggravated the toxicity with a magnitude that ranges between 13.5-18.1% when compared to vehicle treated injured mice. On the other hand, in the APAP model, while mice treated with 40 mg/kg of *Poria* showed 4.3% inhibition in serum ALT when compared to the vehicle control, the other components increase the liver damage within a range of 6.8-33.1%.

TABLE 11

Dose-correlated liver protection of the composition MAP AND MAS in APAP/CCL4-induced hepatotoxicity model

| Material | Dose/code | N | Dose (mg/kg) M/A/P or S | APAP (400 mg/kg) | | | CCL4 (25 µL/kg) | | |
|---|---|---|---|---|---|---|---|---|---|
| | | | | % Change | P-values | Survival rate | % Change | P-values | Survival rate |
| Control (—) | — | 5 | 0 | — | — | 100 | — | — | 100 |
| APAP/CCL4 | — | 10 | 0 | — | — | 60 | — | — | 100 |
| Composition | 200 | 10 | 32/128/40 | 25.8 | 0.49 | 50 | 66.9 | 0.0015 | 100 |

TABLE 11-continued

Dose-correlated liver protection of the composition MAP AND MAS in APAP/CCL4-induced hepatotoxicity model

| Material | Dose/ code | N | M/A/ P or S | APAP (400 mg/kg) | | | CCL4 (25 µL/kg) | | |
|---|---|---|---|---|---|---|---|---|---|
| | | | | % Change | P- values | Survival rate | % Change | P- values | Survival rate |
| #MAP2 | 300 | 10 | 48/192/60 | 62.9 | 0.01 | 90 | 80.0 | 0.0002 | 100 |
| (1:4) 20% | 400 | 10 | 64/256/80 | 88.1 | 0.0001 | 100 | 83.7 | 0.0002 | 100 |
| Composition | 200 | 10 | 32/128/40 | 32.4 | 0.16 | 70 | 54.1 | 0.0109 | 100 |
| #MAS2 | 300 | 10 | 48/192/60 | 62.7 | 0.02 | 80 | 74.9 | 0.0004 | 100 |
| (1:4) 20% | 400 | 10 | 64/256/80 | 78.7 | 0.0007 | 100 | 79.7 | 0.0002 | 100 |
| *Myristica* | M (R603) | 10 | 32 | −33.1 | 0.38 | 60 | 40.7 | 0.03 | 100 |
| *Astragalus* | A (L497) | 10 | 128 | −19.6 | 0.56 | 40 | −18.1 | 0.38 | 100 |
| *Poria* | P (L501) | 10 | 40 | 4.3 | 0.89 | 40 | −13.5 | 0.52 | 100 |
| *Schisandra* | S (L499) | 10 | 40 | −6.8 | 0.84 | 30 | −16.7 | 0.39 | 100 |

Example 17: Evaluation of the Synergy for MAP and MAS Compositions

A widely used synergy calculation equation, the Colby's equation (Colby, 1967) was utilized to evaluate the benefit of combining *Myristica fragrance, Astragalus membranaceus, Poria cocos* and *Schizandra chinensis*, in both APAP and CCL4 model. In this method, for a formulation of two or more materials together will presumed to have a synergy, if the observed values of a certain end point measurement is greater or equal to the hypothetically calculated values. As seen in the Table 12 below, in the current study the observed values were greater than the expected theoretical values in either models indicating the existence of synergy in formulating three ingredients at a specific ratio to yield in compositions MAP or MAS. The merit of putting *Myristica fragrance, Astragalus membranaceus,* and *Poria cocos* or *Myristica fragrance, Astragalus membranaceus* and *Schizandra chinensis* was confirmed by their unexpected enhanced protection of the liver damage caused by APAP or CCL4.

TABLE 12

Unexpected synergistic activity of *Myristica fragrance, Astragalus membranaceus, Poria cocos,* and *Schizandra chinensis* in liver protection.

| Dose (mg/kg) | Materials/Equation | % Inhibitions | | | |
|---|---|---|---|---|---|
| | | APAP | | CCL4 | |
| | | MAP | MAS | MAP | MAS |
| 32 | *Myristica* | −33.1 | −33.1 | 40.7 | 40.7 |
| 128 | *Astragalus* | −19.6 | −19.6 | −18.1 | −18.1 |
| 40 | *Poria/Schizandra* | 4.3 | −6.8 | −13.5 | −16.7 |
| | (x + y + Z) = A | −48.4 | −59.5 | 9.1 | 5.9 |
| | (xyz)/10000 = B | 0.3 | −0.4 | 1.0 | 1.2 |
| | ((xy) + (xz) + (yz))/100 = C | 4.2 | 10.1 | −10.4 | −11.1 |
| 200 | Expected (MAP/MAS) | −52.3 | −70.0 | 20.5 | 18.3 |
| | Observed (MAP/MAS) | 25.8 | 32.4 | 66.9 | 54.1 |

Note:
(−: negative) values indicate increase in severity of liver damage.

Example 18: Efficacy Confirmation Study of the MAP and MAS Compositions in CCL4-Induced Hepatotoxicity Models Once consistent liver protection activity of compositions MAP and MAS in both APAP and CCL4 models were documented, additional comprehensive confirmatory study was carried out using the CCL4 induced hepatotoxicity model. Mice were gavaged with the composition MAS or MAS at doses of 150, 200 and 300 mg/kg orally. Milk thistle at a dose of 200 mg/kg was included as a reference. 10% tween 20 was used as a carrier vehicle for all the materials. Control mice received tween 20 only. Besides serum Alanine transaminase (ALT), Liver panel such as Total protein, Total bilirubin, direct and indirect bilirubin, albumin, globulin, Aspartate transaminase (AST), bile acid, Alkaline phosphatase (ALP) and γ-glutamyl transferase (GTT) were measured for control, CCL4, Milk thistle, MAP (150, 200 and 300 mg/kg), and MAS (150, 200, and 300 mg/kg) at T24.

As seen in Tables 13 and 14 below, clear dose-correlated inhibitions in many of the major liver toxicity indicator biomarkers. While both compositions (MAP and MAS) exhibited significant liver protection activities, the composition MAS showed slightly stronger efficacy than the composition MAP. Given these substantial moderations of data for vital biomarkers, it can be inferred that, the minimum efficacious dosage for both the compositions could be 150 mg/kg. Staying with similar methods of composition efficacy analysis, the composition MAP resulted in 30.8-71.1% inhibitions in ALT and 41.7-75.7% inhibitions in AST when compared to vehicle treated injured mice. Similarly, 47.5-82.6% inhibitions in ALT and 55.6-85.4% inhibitions in AST were observed for the composition MAS when compared to vehicle treated injured mice. Overall, the compositions MAP and MAS provided greater protection to liver damage in multiple frequently monitored liver biomarkers.

TABLE 13

Summary of Liver panel analyte levels for mice treated with MAP/MAS, in CCL4-induced hepatotoxicity model.

| Analyte | Control | CCL4 (25 µl/kg) | Milk thistle (200 mg/kg) | MAP (mg/kg) | | |
|---|---|---|---|---|---|---|
| | | | | 150 | 200 | 300 |
| ALT | 171 ± 3.1 | 11238.4 ± 4980.6 | 10894.9 ± 2000.4 | 7781.5 ± 2236.4* | 5072.9 ± 1772.9† | 3244.6 ± 1440.6‡ |
| AST | 58.3 ± 12.0 | 6981.9 ± 3386.0 | 6726.3 ± 1698.9 | 4067.4 ± 1564.8* | 2427.1 ± 1565.9‡ | 1700.0 ± 996.9‡ |
| Bile acid | 1.0 ± 0.0 | 48.8 ± 28.3 | 23.9 ± 7.2* | 24.3 ± 15.1* | 21.4 ± 34.1* | 19.1 ± 36.6* |
| GTT | 0.2 ± 0.4 | 1.3 ± 0.7 | 1.1 ± 0.3 | 1.3 ± 1.2 | 1.3 ± 0.8 | 0.8 ± 0.4 |
| ALP | 79.7 ± 18.2 | 119.0 ± 26.9 | 131.6 ± 34.4 | 99.2 ± 21.4 | 76.7 ± 16.0‡ | 71.4 ± 21.6‡ |
| T.bilirubin | 0.1 ± 0.0 | 0.3 ± 0.1 | 0.4 ± 0.1 | 0.3 ± 0.1* | 0.3 ± 0.1 | 0.2 ± 0.1‡ |
| D.bilirubin | 0.0 ± 0.0 | 0.1 ± 0.0 | 0.1 ± 0.0 | 0.1 ± 0.1 | 0.0 ± 0.0† | 0.0 ± 0.0* |
| I.bilirubin | 0.1 ± 0.0 | 0.3 ± 0.1 | 0.3 ± 0.1 | 0.2 ± 0.0 | 0.2 ± 0.1 | 0.2 ± 0.1* |
| T.protein | 4.4 ± 0.2 | 4.8 ± 0.2 | 4.7 ± 0.2 | 4.6 ± 0.1* | 4.6 ± 0.3* | 4.5 ± 0.2† |
| Albumin | 2.3 ± 0.1 | 2.7 ± 0.2 | 2.7 ± 0.1 | 2.6 ± 0.1* | 2.6 ± 0.2* | 2.5 ± 0.1‡ |
| Globulin | 2.1 ± 0.1 | 2.1 ± 0.1 | 2.0 ± 0.2 | 2.0 ± 0.1 | 2.0 ± 0.1 | 2.1 ± 0.1 |

| Analyte | MAS (mg/kg) | | |
|---|---|---|---|
| | 150 | 200 | 300 |
| ALT | 5904.5 ± 3158.7* | 2747.3 ± 1906.4‡ | 1957.4 ± 689.5‡ |
| AST | 3097.4 ± 1921.8† | 1260.8 ± 749.9‡ | 1017.1 ± 415.9‡ |
| Bile acid | 14.8 ± 6.0† | 9.3 ± 3.9‡ | 7.8 ± 2.2‡ |
| GTT | 1.1 ± 0.7 | 0.6 ± 0.5* | 0.6 ± 0.5* |
| ALP | 93.5 ± 28.0* | 81.3 ± 23.6† | 74.9 ± 19.9‡ |
| T.bilirubin | 0.2 ± 0.1* | 0.2 ± 0.1* | 0.2 ± 0.1‡ |
| D.bilirubin | 0.1 ± 0.0 | 0.0 ± 0.0* | 0.0 ± 0.1* |
| I.bilirubin | 0.2 ± 0.1* | 0.2 ± 0.1* | 0.2 ± 0.0† |
| T.protein | 4.7 ± 0.2 | 4.8 ± 0.2 | 4.6 ± 0.7 |
| Albumin | 2.5 ± 0.1* | 2.5 ± 0.1* | 2.5 ± 0.2† |
| Globulin | 2.2 ± 0.2 | 2.2 ± 0.1* | 2.2 ± 0.4 |

*P ≤0.05;
†P ≤0.001;
‡P ≤0.0001

TABLE 14

Summary of percent changes of liver panel markers from MAP/MAS group compared to vehicle treated mice in CCL4 model.

| Analyte | Milk thistle (200 mg/kg) | MAP (mg/kg) | | | MAS (mg/kg) | | |
|---|---|---|---|---|---|---|---|
| | | 150 | 200 | 300 | 150 | 200 | 300 |
| ALT | 3.1↓ | 30.8 | 54.9 | 71.1 | 47.5 | 75.6 | 82.6 |
| AST | 3.7 | 41.7 | 65.2 | 75.7 | 55.6 | 81.9 | 85.4 |
| Bile acid | 50.9 | 50.3 | 56.1 | 60.9 | 69.6 | 81.0 | 83.9 |
| GTT | 13.3 | -6.7 | 0.0 | 40.0 | 12.7 | 53.3 | 53.3 |
| ALP | -10.6↑ | 16.7 | 35.6 | 40.0 | 21.4 | 31.7 | 37.0 |
| T.bilirubin | -20.0 | 20.0 | 22.5 | 37.5 | 26.4 | 30.0 | 55.0 |
| D.bilirubin | 0.0 | 33.3 | 77.8 | 66.7 | 15.2 | 55.6 | 66.7 |
| I.bilirubin | -25.8 | 16.1 | 6.5 | 29.0 | 29.6 | 22.6 | 38.7 |
| T.protein | 3.3 | 4.3 | 5.0 | 5.7 | 2.2 | 1.0 | 5.0 |
| Albumin | 1.2 | 4.6 | 6.1 | 9.2 | 6.6 | 6.4 | 8.0 |
| Globulin | 6.0 | 4.0 | 3.6 | 1.2 | -3.5 | -6.0 | -2.4 |

(+): ↓Decrease from APAP/CCL4 (+) vehicle
(-): ↑Increase from APAP/CCL4 (+) vehicle Example 19: Liver Protection Effects of MAP Compositions in Acute Ethanol-Induced Liver Toxicity Models Model Inductions: The hepatoprotective activity of the MAP composition was assessed using acute alcohol induced liver toxicity model for "binge drinking". In this study, male CD-1 mice weighing 18-24 g, were purchased at the age of week 8 (Charles River Laboratories, Inc., Wilmington, Mass.) and acclimated for one week. Animals received a total of 4 doses of the composition at oral doses of 300 mg/kg. Dosage selection was made based on previously conducted acetaminophen (APAP) and Carbon tetrachloride (CCl4)-induced liver toxicity models. Mice were pre-treated with three oral doses of MAP or Silymarin followed by gavaging with ethanol (lot #: SHBG1307V, Sigma, St. Louis, Mo.) at 50% in 12 ml/kg dosing volume and then every 12 hours thereafter for a total of 3 doses [69]. The last oral treatment dose was given between the second and the third ethanol administration. Mice were fasted for 12 hours after the last dose of ethanol for serum and tissue collection. Silymarin (Product Number: S0292; Lot #BCBJ0393V; Sigma, Saint Louis, Mo.) was used as a positive control in this study at oral doses of 200 mg/kg. Control mice without Ethanol received carrier vehicle only. 10% Tween-20 (Lot #0134C141 from Amresco, Solon, Ohio), was used as a carrier vehicle for all the tested materials. Control mice without Ethanol received carrier vehicle only. Liver tissues were collected immediately after necropsy and were kept in dry ice until transferred to −80° C. freezer. Materials were then shipped to a contract laboratory (Brunswick Laboratories, 200 Turnpike Rd, MA 01772, USA) in dry ice for final specimen processing and biomarkers (SOD, GSH and TG) analysis. Portion of the liver, the left lobe from each mouse was fixed in 10% buffered formaldehyde and sent to Nationwide Histology (Veradale, Wash.) for tissue processing and histological examination.

Example 20: Effect of MAP on Liver Functions From Acute Ethanol-Induced Liver Toxicity Models Serum was isolated from blood drawn at T24 using serum separator tube after 30 minute room temperature clot and spun at 3000 rpm for 10 minutes for ALT (alanine aminotransferase), AST (aspartate aminotransferase), total protein, albumin, total bilirubin, Cholesterol (CHOL), Triglyceride (TRIG), High-density lipoprotein (HDL) and Low-density lipoprotein (LDL) monitoring in an automated colorimetric assay using Beckman Coulter AU2700 at Phoenix Laboratories (Everett, Wash.).

Significant elevations in the serum level of ALT and AST in animals often reflects liver injury [70]. As seen in Table 15, ALT and AST were both found to be elevated significantly in mice treated with alcohol alone demonstrating the induction of acute alcohol-induced liver injury. Excessive increases of these markers were significantly inhibited at 46.3% (ALT) and 43.6% (AST) when mice were treated with MAP at oral dose of 300 mg/kg for a total of 4 consecutive days. The live protection activity of MAP was also supported by the statistically significant increase in serum albumin and total protein production (Table 15). These results validate that the composition protects the liver against acute alcohol-induced insult. At lease in this study, no significant changes in all the serum parameters monitored were observed for mice treated with Silymarin at the dose of 200 mg/kg (Table 15).

and xanthine, and the activity of SOD in a given sample is quantified by the standard curve generated using the SOD standards. One unit of SOD is defined as the amount of enzyme needed to exhibit 50% dismutation of superoxide radicals. A Superoxide Dismutase Assay Kit from CAYMAN Chemical Co., Inc. (Ann Arbor, Mich.) was used for analysis. The protein concentrations of the tissue homogenates were determined by assessing protein concentrations of the suppressants via a Pierce™ BCA Protein Assay Kit. D) Triglyceride Analysis-triglycerides were detected by a cascade of enzymatic reactions involving lipoprotein lipase, glycerol kinase, glycerol-3-phosphate oxidase, and glycerol-3-phosphate peroxidase that results in the formation of a colorometrically detected product (540 nm), quinoneimine. A Triglyceride Assay Kit from CAYMAN Chemical Co., Inc. (Ann Arbor, Mich.) was used for this analysis. E) Materials and Equipment—Homogenizer (cat no TH-01) from Omni International (Kennesaw, Ga.); Hard Tissue Omni Tip™ Plastic Homogenizing Probes (7 mm×110 mm) from Omni International (Kennesaw, Ga.); Refrigerated Centrifuge (model no 5402) from Eppendorf (Hauppauge, N.Y.); Microplate Reader (model no. Synergy HT) from Biotek (Shoreline, Wash.) were used.

TABLE 15

Clinical chemistry output as a measure for hepatic functions

| Group (N = 12) | Dose (mg/kg) | ALT (mg/dL) | AST (mg/dL) | ALBUMIN (g/dL) | T.PRTN (g/dL) | T.BIL (mg/dL) |
| --- | --- | --- | --- | --- | --- | --- |
| Control | 0 | 19.1 ± 1.6* | 49.8 ± 7.1* | 2.58 ± 11* | 4.69 ± 0.13* | 0.18 ± 0.04* |
| Ethanol | 0 | 38.7 ± 8.7 | 109.3 ± 17.7 | 2.08 ± 0.21 | 4.02 ± 0.31 | 0.14 ± 0.05 |
| Silymarin | 200 | 32.3 ± 4.7 | 84.8 ± 9.4 | 2.12 ± 0.24 | 4.15 ± 0.28 | 0.14 ± 0.05 |
| MAP | 300 | 20.8 ± 0.9* | 61.6 ± 5.8* | 2.28 ± 0.23* | 4.42 ± 0.38* | 0.13 ± 0.05 |

| Group (N = 12) | Dose (mg/kg) | CHOL (mg/dL) | TRIG (mg/dL) | HDL (mg/dL) | LDL (mg/dL) |
| --- | --- | --- | --- | --- | --- |
| Control | 0 | 181.3 ± 29.8* | 121.3 ± 30.5* | 85.4 ± 8.7* | 12.23 ± 3.08 |
| Ethanol | 0 | 150.8 ± 26.0 | 200.9 ± 69.8 | 64.1 ± 15.7 | 11.90 ± 1.91 |
| Silymarin | 200 | 163.7 ± 27.1 | 160.2 ± 76.9 | 69.1 ± 14.8 | 13.09 ± 3.48 |
| MAP | 300 | 174.6 ± 32.0 | 200.8 ± 74.8 | 79.4 ± 13.7* | 14.92 ± 4.66 |

Data are expressed as Mean ± SD.
*P-values Vs Ethanol ≤0.05.

Example 21: Effect of MAP on Oxidative Stress Biomarkers (GSH and SOD) and Triglyceride Content in Liver Homogenates From Acute Ethanol-Induced Liver Toxicity Models Glutathione (GSH), Superoxide dismutases (SODs) and Triglyceride (TG) measurements: A) Sample Preparation-Frozen tissue was ground to a course powder using a pulverizer. 1 mL of PBS (Phosphate-buffered saline) containing 19.6 μM EDTA (Ethylenediaminetetraacetic acid) was added to ~0.2 g of ground tissue, and homogenized for 1 min in ice bath using a homogenizer from Omni International. The mixture was then centrifuged for 15 min at 10,000 rpm at 4° C. A portion of the supernatant was used for SOD, triglyceride, and protein analysis. The rest of supernatant was further processed for GSH analysis. B) For GSH analysis, a portion of the supernatant was mixed with the same volume of 100 mg/mL mercaptopropionic acid (MPA) solution to deproteinize in order to avoid interference from proteins. The mixture was let stand at room temperature for 5 min after vortexing, then centrifuged for 15 min at 10,000 rpm at 4° C. The deproteinated supernatant was evaluated for GSH content using a Glutathione Assay Kit from CAYMAN Chemical Co., Inc. (Ann Arbor, Mich.) C) SOD analysis-The SOD assay is a colorimetric assay, which utilizes a tetrazolium salt to measure the dismutation of superoxide radicals that were induced by xanthine oxidase Glutathione is one of the phase II antioxidant enzymes that protect cells against endogenous or exogenous chemical insults and their reactive oxygen species by-products where its excessive depletion can induce oxidative stress and liver injury. As depicted in Table 16, liver tissue total glutathione levels were found significantly higher in animals treated with the composition MAP. Increased level of GSH was also noted for mice treated with alcohol and the vehicle control compared to the normal control mice. It has previously been reported for fasted animals to have lower level of GSH [71]. Meanwhile, 12 h after the last ethanol administration, the ethanol group had significantly decreased SOD activities to 36.9% compared to the normal control. As seen in Table 16, MAP replenished the depleted superoxide dismutase by more than 60% (compared to Ethanol group). In fact, the increase in SOD level was comparable to that of the normal control animals without liver toxicity induction. These increases of phase II enzymes substantiate each other to provide the strong anti-oxidant activity of the MAP composition. Additionally, ethanol administration induced significant accumulation of TG in the liver (Table 16). MAP oral treatment obviously inhibited the increase of hepatic TG levels by 12%, and the effects of MAP were comparable to those of observed for the normal control mice (Table 16). These results indicate that MAP might be effective against alcoholic steatosis.

TABLE 16

Effect of MAP on Liver Oxidative BioMarkers

| Compound | GSH [nmol/mg protein] | SOD [U/mg protein] | TG [µg/mg protein] |
|---|---|---|---|
| Normal Control | 15.13 ± 1.51 | 52.30 ± 9.49 | 20.00 ± 2.94 |
| Ethanol (50%, 12 ml/kg) | 28.39 ± 4.25 | 33.01 ± 7.1 | 25.16 ± 2.81 |
| MAP (300 mg/kg) | 32.52 ± 4.56* | 53.19 ± 9.37† | 22.11 ± 2.47 |

*P-values Vs Control ≤ 0.000001.
†60% increase in SOD compared to ethanol exposed vehicle treated mice.

Example 22: Anti-Alcoholic Steatohepatitis (ASH) activity of MAP from Acute Ethanol-Induced Liver Toxicity Models Liver tissues from normal control (N=12), Ethanol+vehicle (N=10), and Ethanol+MAP (300 mg/kg, N=12) treated groups were fixed in 10% buffered formaldehyde and embedded in paraffin wax for histological examination. Specimens were processed on a Shandon Excelsior ES tissue processor using graded alcohols and xylenes on an overnight cycle. The tissues were then cut at 4 microns and stained using a progressive hematoxylin and eosin stain using a sakura DRS-601 slide stainer. The entire stained field were assessed for any cellular and structural changes under multiple magnification and subjected to histopathological scoring using modified Non-Alcoholic Steatohepatitis (NASH) Clinical Research Network [72] for ballooning degenerations (severity score 0-4), microvascular steatosis (severity score 0-4), cytoplasmic condensation (severity score 0-4), hepatocyte vacuolation (severity score 0-4), and necrosis (severity score 0-4).

The liver tissues of the untreated control animals showed normal architecture of hepatic cells with clear cytoplasm, normal kupffer cells and normal large nuclei. In the vehicle treated ethanol-challenged mice, the liver tissue showed distorted architecture with extensive area of hepatic steatosis, cytoplasmic condensation and marked nuclei shrinkage. Some degenerative ballooning, vacuolation and periportal inflammation were also observed in these groups. On the other hand, discernible normal cellular architecture, lesser degrees of structural changes were evident in mice treated with MAP (Table 17). As seen in Table 17, MAP showed statistically significant reduction in ballooning degeneration, micro and macro vascular steatosis, cytoplasmic or nuclear condensation and shrinkage as well as periportal and perinecrotic inflammations when compared to vehicle treated alcohol induced disease model. The alcoholic steatohepatitis score (ASH Score) were then determined using these quantitative values. Compiling these histopathology findings together lead to statistically significant decrease in the alcoholic Steatohepatitis score for mice orally treated with 300 mg/kg MAP composition in comparison to that of the Ethanol group (Table 18).

TABLE 17

H&E staining analysis liver tissues from mice treated with MAP in the ethanol-induced hepatotoxicity mode

| Histopathology changes | Control + Vehicle $^a$ (N = 12) | Ethanol + Vehicle (50%, 12 ml/kg) (N = 10)† | Ethanol + MAP (300 mg/kg) (N = 12) |
|---|---|---|---|
| Ballooning | 0.00 ± 0.00 | 0.30 ± 0.24 | 0.00 ± 0.00** |
| Steatosis | 0.00 ± 0.00 | 1.45 ± 0.65 | 0.46 ± 0.48** |
| Condensation | 0.04 ± 0.14 | 0.30 ± 0.33 | 0.00 ± 0.00** |
| Vacuolation | 0.08 ± 0.19 | 0.40 ± 0.30 | 0.38 ± 0.22 |
| Necrosis | 0.00 ± 0.00 | 0.10 ± 0.20 | 0.04 ± 0.14 |
| Inflammation | 0.00 ± 0.00 | 0.15 ± 0.23 | 0.00 ± 0.00* |

$^a$ Vehicle - 10% Tween 20.
*P -values Verses Ethanol ≤ 0.05;
**P -values Verses Ethanol ≤ 0.001;
†Two mice were found deceased in the ethanol + vehicle treated group.

TABLE 18

Alcoholic Steatohepatitis (ASH) Score

| Group | N | Mean | SD | P-values† |
|---|---|---|---|---|
| Control | 12 | 0.13 | 0.32 | 0.000001 |
| Ethanol (50%, 12 ml/kg) | 10 | 2.7 | 1.96 | — |
| MAP (300 mg/kg) | 12 | 0.88 | 0.83 | 0.0001 |

†P-values were Vs vehicle treated Ethanol

Thus, specific embodiments and methods of compounds and compositions useful for liver health management, including stereoisomers, pharmaceutically or nutraceutically acceptable salts, tautomers, glycosides and prodrugs of the disclosed compounds, along with related methods of improving and maintaining liver health have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

REFERENCES

Each of the below-listed references are the full citations of the references already disclosed herein. It should be noted that each of these references is incorporated herein by reference in its entirety.

1. Agyemang K, Han L, Liu E, Zhang Y, Wang T, Gao X. Recent Advances in *Astragalus membranaceus* Anti-Diabetic Research: Pharmacological Effects of Its Phytochemical Constituents. Evid Based Complement Alternat Med. 2013; 2013:654643.
2. Ajith T A, Hema U, Aswathy M S. Zingiber officinale Roscoe prevents acetaminophen-induced acute hepatotoxicity by enhancing hepatic antioxidant status. Food Chem. Toxicol. 2007; 45:2267-2272.
3. Albano E., Lott A. K., Slater T. F., Stier A., Symons M. C. R., and Tomasi A. (1982) Spin trapping studies on the free radical products formed by metabolic activation of carbon tetrachloride in rat liver microsomal fractions, isolated hepatocytes and in vivo. Biochem. J. 204:593-603.
4. Bajt M L, Cover C, Lemasters J J, Jaeschke H. Nuclear translocation of endonuclease G and apoptosis inducing factor during acetaminophen-induced liver cell injury. Toxicol. Sci. 2006; 94:217-225.
5. Bajt M L, Farhood A, Lemasters J J, Jaeschke H. Mitochondrial bax translocation accelerates DNA fragmentation and cell necrosis in a murine model of acetaminophen hepatotoxicity. J. Pharmacol. Exp. Ther. 2008; 324:8-14.
6. Bajt M L, Ramachandran A, Yan H M, Lebofsky M, Farhood A, Lemasters J J, Jaeschke H. Apoptosis inducing factor modulates mitochondrial oxidant stress in acetaminophen hepatotoxicity. Toxicol. Sci. 2011; 122:598-605.
7. Chamulitrat W., Blazka M. E., Jordan S. J., Luster M. I., and Mason R. P. (1995) Tumor necrosis factor-alpha and nitric oxide production in endotoxin-primed rats administered carbon tetrachloride. Life Sci. 57:2273-2280.
8. Chamulitrat W., Jordan S. J., and Mason R. P. (1994) Nitric oxide production during endotoxic shock in carbon tetrachloride-treated rats. Mol. Pharmacol. 46:391-397.
9. Cheeseman K. H., Davies M. J., Emery S., Maddix S. P., and Slater T. F. (1987) Effects of alpha-tocopherol on carbon tetrachloride metabolism in rat liver microsomes. Free Radic. Res. Commun. 3:325-330.
10. Cheng S1, Eliaz I, Lin J, Thyagarajan-Sahu A, Sliva D. Triterpenes from *Poria cocos* suppress growth and invasiveness of pancreatic cancer cells through the downregulation of MMP-7. Int J Oncol. 2013; 42(6):1869-74.
11. Cho WC1, Leung K N. In vitro and in vivo immunomodulating and immunorestorative effects of *Astragalus membranaceus*. J Ethnopharmacol. 2007; 113(1):132-41.
12. Chung T W, Koo B S, Choi E G, Kim M G, Lee I S, Kim C H: Neuroprotective effect of a chuk-me-sun-dan on neurons from ischemic damage and neuronal cell toxicity. Neurochem Res 2006,31:1-9.
13. Colby, S R. Calculating Synergistic and Antagonistic Responses of Herbicide combinations. Weeds, Vol. 15, No. 1 (January, 1967), pp. 20-22.
14. Composition comprising the extract of combined herbs for preventing and treating liver disease, U.S. Pat. No. 8,986,756 B2
15. Cover C, Mansouri A, Knight T R, Bajt M L, Lemasters J J, Pessayre D, Jaeschke H. Peroxynitrite induced mitochondrial and endonuclease-mediated nuclear DNA damage in acetaminophen hepatotoxicity. J. Pharmacol. Exp. Ther. 2005; 315:879-887.
16. Cuellar M J, Giner R M, Recio M C, Just M J, Mañez S, Rios J L: Effect of the basidiomycete *Poria cocos* on experimental dermatitis and other inflammatory conditions. Chem Pharm Bull (Tokyo) 1997,45:492-494.
17. Czaja M. J., Xu J., and Alt E. (1995) Prevention of carbon tetrachloride-induced rat liver injury by soluble tumor necrosis factor receptor. Gastroenterology 108: 1849-1854.
18. Davern T J 2nd, James L P, Hinson J A, Polson J, Larson A M, Fontana R J, Lalani E, Munoz S, Shakil A O, Lee W M, Acute Liver Failure Study Group. Measurement of serum acetaminophen-protein adducts in patients with acute liver failure. Gastroenterology. 2006; 130:687-694
19. Extract of *artemisia* U.S. Pat. No. 4,442,087 A
20. Fu J, Wang Z, Huang L, Zheng S, Wang D, Chen S, Zhang H, Yang S. Review of the botanical characteristics, phytochemistry, and pharmacology of *Astragalus membranaceus* (Huangqi). Phytother Res. 2014; 28(9):1275-83.
21. Fuchs S M, Heinemann C, Schliemann-Willers S, Härtl H, Fluhr J W, Elsner P: Assessment of anti-inflammatory activity of *Poria cocos* in sodium lauryl sulphate-induced irritant contact dermatitis. Skin Res Technol 2006, 12:223-227.
22. Hanawa N, Shinohara M, Saberi B, Gaarde W A, Han D, Kaplowitz N. Role of JNK translocation to mitochondria leading to inhibition of mitochondria bioenergetics in acetaminophen-induced liver injury. J. Biol. Chem. 2008; 283:13565-13577.
23. Hu Y Q, Tan R X, Chu M Y. Ou W X. Hepatoprotective effect and isolation of polypeptides from *Artemisia capillaris*. Zhongcaoyao 1999; 12(30):894-6
24. Jaeschke H, McGill M R, Ramachandran A. Oxidant stress, mitochondria, and cell death mechanisms in drug-induced liver injury: lessons learned from acetaminophen hepatotoxicity. Drug Metab. Rev. 2012a; 44:88-106.
25. Jaeschke H, Williams C D, McGill M R, Xie Y, Ramachandran A. Models of drug-induced liver injury for evaluation of phytotherapeutics and other natural products. Food Chem Toxicol. 2013 May; 55:279-89.
26. Jaeschke H. Glutathione disulfide formation and oxidant stress during acetaminophen-induced hepatotoxicity in mice in vivo: the protective effect of allopurinol. J. Pharmacol. Exp. Ther. 1990; 255:935-941.
27. James L P, Letzig L, Simpson P M, Capparelli E, Roberts D W, Hinson J A, Davern T J, Lee W M. Pharmacokinetics of acetaminophen-protein adducts in adults with acetaminophen overdose and acute liver failure. Drug Metab. Dispos. 2009; 37:1779-1784.
28. Ji L, Jiang P, Lu B, Sheng Y, Wang X, Wang Z. Chlorogenic acid, a dietary polyphenol, protects acetaminophen-induced liver injury and its mechanism. J Nutr Biochem. 2013; 24(11):1911-9.
29. Jollow D J, Mitchell J R, Potter W Z, Davis D C, Gillette J R, Brodie B B. Acetaminophen-induced hepatic necrosis. II. Role of covalent binding in vivo. J. Pharmacol. Exp. Ther. 1973; 187:195-202.
30. Kikuchi T, Uchiyama E, Ukiya M, Tabata K, Kimura Y, Suzuki T, Akihisa T: Cytotoxic and apoptosis-inducing activities of triterpene acids from *Poria cocos*. J Nat Prod 2011, 74:137-144.
31. Kon K, Kim J S, Jaeschke H, Lemasters J J. Mitochondrial permeability transition in acetaminophen induced necrosis and apoptosis of cultured mouse hepatocytes. Hepatology. 2004; 40:1170-1179.
32. Larson A M. Acetaminophen hepatotoxicity. Clin. Liver Dis. 2007; 11:525-548.
33. Lee H S, Kim H H, Ku S K. Hepatoprotective effects of *Artemisiae capillaris* herba and *Picrorrhiza rhizoma* combinations on carbon tetrachloride-induced subacute liver damage in rats. Nutr Res. 2008; 28(4):270-7.
34. Lee K Y, Jeon Y J. Macrophage activation by polysaccharide isolated from *Astragalus membranaceus*. Int Immunopharmacol. 2005; 5(7-8):1225-33.
35. Lee S M, Lee Y J, Yoon J J, Kang D G, Lee H S: Effect of *Poria cocos* on hypertonic stress-induced water channel expression and apoptosis in renal collecting duct cells. J Ethnopharmacol 2012, 141:368-376.
36. Liu W, Gao F F, Li Q, Lv J W, Wang Y, Hu P C, Xiang Q M, Wei L. Protective effect of *astragalus* polysaccharides on liver injury induced by several different chemotherapeutics in mice. Asian Pac J Cancer Prev. 2014; 15(23):10413-20.

37. Loguidice A, Boelsterli U A. Acetaminophen overdose-induced liver injury in mice is mediated by peroxynitrite independently of the cyclophilin D-regulated permeability transition. Hepatology. 2011; 54:969-978.
38. Luckey S W and Petersen D R. (2001) Activation of Kupffer cells during the course of carbon tetrachloride-induced liver injury and fibrosis in rats. Exp. Mol. Pathol. 71:226-240.
39. Masubuchi Y, Suda C, Horie T. Involvement of mitochondrial permeability transition in acetaminophen-induced liver injury in mice. J. Hepatol. 2005; 42:110-116.
40. McGill M R, Sharpe M R, Williams C D, Taha M, Curry S C, Jaeschke H. The mechanism underlying acetaminophen-induced hepatotoxicity in humans and mice involves mitochondrial damage and nuclear DNA fragmentation. J. Clin. Invest. 2012a; 122:1574-1583.
41. McGill M R, Williams C D, Xie Y, Ramachandran A, Jaeschke H. Acetaminophen-induced liver injury in rats and mice: Comparison of protein adducts, mitochondrial dysfunction, and oxidative stress in the mechanism of toxicity. Toxicol. Appl. Pharmacol. 2012b; 264:387-394.
42. Mitchell J R, Jollow D J, Potter W Z, Davis D C, Gillette J R, Brodie B B. Acetaminophen-induced hepatic necrosis. I. Role of drug metabolism. J. Pharmacol. Exp. Ther. 1973; 187:185-194.
43. Morita T, Jinno K, Kawagishi H, Arimoto Y, Suganuma H, Inakuma T, et al. Hepatoprotective Effect of Myristicin from Nutmeg (*Myristica fragrans*) on Lipopolysaccharide/D-Galactosamine-Induced Liver Injury. J Agric Food Chem. 2003; 51:1560-5.
44. Nakagawa H, Maeda S, Hikiba Y, Ohmae T, Shibata W, Yanai A, Sakamoto K, Ogura K, Noguchi T, Karin M, Ichijo H, Omata M. Deletion of apoptosis signal-regulating kinase 1 attenuates acetaminophen-induced liver injury by inhibiting c-Jun N-terminal kinase activation. Gastroenterology. 2008; 135:1311-21.
45. Nelson S. D. and Harrison P. J. (1987) Roles of cytochrome P450 in chemically induced cytotoxicity. In: Guengrich F. P. (Ed.), Mammalian Cytochromes P450, CRC Press, Boca Raton, pp. 19-80.
46. Park Y H, Son I H, Kim B, Lyu Y S, Moon H I, Kang H W: *Poria cocos* water extract (PCW) protects PC12 neuronal cells from beta-amyloid-induced cell death through antioxidant and antiapoptotic functions. Pharmazie 2009, 64:760-764.
47. Poyer J. L., McCay P. B., Lai E. K., Janzen E. G., and Davis E. R. (1980) Confirmation of assignment of trichloromethyl radical spin adduct detected by spin trapping during 13C carbon tetrachloride metabolism in vitro and in vivo. Biochem. Biophys. Res. Commun. 94:1154-1160.
48. Qiu Y, Benet L Z, Burlingame A L. Identification of hepatic protein targets of the reactive metabolites of the non-hepatotoxic regioisomer of acetaminophen, 3'-hydroxyacetanilide, in the mouse in vivo using two-dimensional gel electrophoresis and mass spectrometry. Adv. Exp. Med. Biol. 2001; 500:663-673.
49. Ramachandran A, Lebofsky M, Baines C P, Lemasters J J, Jaeschke H. Cyclophilin D deficiency protects against acetaminophen-induced oxidant stress and liver injury. Free Radic. Res. 2011a; 45:156-164.
50. Ren S, Zhang H, Mu Y, Sun M, Liu P. Pharmacological effects of Astragaloside IV: a literature review. J Tradit Chin Med. 2013; 33(3):413-6.
51. Renner H. (1985) The limited relevance of models used for testing human hepatic diseases and their prevention. In: Keppler E., Popper H., Bianchi L., and Reutter W. (Eds.), Mechanisms of Hepatocyte Injury and Death, MTP Press Ltd., Lancaster, pp. 311-320.
52. Reynolds E. S. (1963) Liver parenchymal cell injury. I. Initial alterations of the cell following poisoning with carbon tetrachloride. J. Cell Biol. 19:139-157.
53. Ríos JL1. Chemical constituents and pharmacological properties of *Poria cocos*. Planta Med. 2011; 77(7):681-91.
54. Sagar S M, Yance D, Wong R K: Natural health products that inhibit angiogenesis: a potential source for investigational new agents to treat cancer-Part 1. Curr Oncol 2006,13:14-26.
55. Saito C, Lemasters J J, Jaeschke H. c-Jun N-terminal kinase modulates oxidant stress and peroxynitrite formation independent of inducible nitric oxide synthase in acetaminophen hepatotoxicity. Toxicol. Appl. Pharmacol. 2010a; 246:8-17.
56. Shao B M, Xu W, Dai H, Tu P, Li Z, Gao X M. A study on the immune receptors for polysaccharides from the roots of *Astragalus membranaceus*, a Chinese medicinal herb. Biochem Biophys Res Commun. 2004; 320(4): 1103-11.
57. Slater T F (1981) Activation of carbon tetrachloride: chemical principles and biological significance. In: McBrien D. C. H., Slater T. F. (Eds.), Free Radicals, Lipid Peroxidation and Cancer, Academic Press, London, pp. 243-270.
58. Tirmenstein M A, Nelson S D. Subcellular binding and effects on calcium homeostasis produced by acetaminophen and a nonhepatotoxic regioisomer, 3'-hydroxyacetanilide, in mouse liver. J. Biol. Chem. 1989; 264:9814-9819.
59. Wan Y, Wu Y L, Lian L H, Nan J X. Protective effect of Ornithogalum saundersiae Ait (Liliaceae) against acetaminophen-induced acute liver injury via CYP2E1 and HIF-1α. Chin. J. Nat. Med. 2012; 10:177-184.
60. Weddle C C, Hornbrook K R, McCay P B. Lipid peroxidation and alteration of membrane lipids in isolated hepatocutes exposed to carbon tetrachloride. J. Biol. Chem. 1976; 251:4973-4978.
61. Wu S J, Ng L T, Lin C C: Antioxidant activities of some common ingredients of traditional chinese medicine, *Angelica sinensis, Lycium barbarum* and *Poria cocos*. Phytother Res 2004,18:1008-1012.
62. Yance D R Jr, Sagar S M: Targeting angiogenesis with integrative cancer therapies. Integr Cancer Ther 2006,5: 9-29.
63. Yang B, Xiao B, Sun T. Antitumor and immunomodulatory activity of *Astragalus membranaceus* polysaccharides in H22 tumor-bearing mice. Int J Biol Macromol. 2013; 62:287-90.
64. Yang C C, Fang J Y, Hong T L, Wang T C, Zhou Y E, Lin T C. Potential antioxidant properties and hepatoprotective effects of an aqueous extract formula derived from three Chinese medicinal herbs against CCl(4)-induced liver injury in rats. Int Immunopharmacol. 2013; 15(1): 106-13.
65. Yasukawa K, Kaminaga T, Kitanaka S, Tai T, Nunoura Y, Natori S, Takido M: 3 beta-p-hydroxybenzoyldehydrotumulosic acid from *Poria cocos*, and its anti-inflammatory effect. Phytochemistry 1998,48:1357-1360.
66. Zaher H, Buters J T, Ward J M, Bruno M K, Lucas A M, Stern S T, Cohen S D, Gonzalez F J. Protection against acetaminophen toxicity in CYP1A2 and CYP2E1 double-null mice. Toxicol. Appl. Pharmacol. 1998; 152:193-199.
67. Zhang L, Ravipati A S, Koyyalamudi S R, Jeong S C, Reddy N, Bartlett J, Smith P T, de la Cruz M, Monteiro M C, Melguizo A, Jiménez E, Vicente F: Anti-fungal and anti-bacterial activities of ethanol extracts of selected traditional Chinese medicinal herbs. Asian Pac J Trop Med 2013,6:673-681.
68. Zhou L, Zhang Y, Gapter L A, Ling H, Agarwal R, Ng K Y: Cytotoxic and antioxidant activities of lanostane-type triterpenes isolated from Poria cocos. Chem Pharm Bull (Tokyo) 2008,56:1459-1462.
69. Carson E J, Pruett S B: Development and characterization of a binge drinking model in mice for evaluation of the immunological effects of ethanol. Alcohol Clin Exp Res. 1996; 20(1):132-8.
70. McGovern A J, Vitkovitsky I V, Jones D L, Mullins M E: Can AST/ALT ratio indicate recovery after acute paracetamol poisoning? Clin Toxicol (Phila). 2015; 53(3): 164-7.
71. Vogt B L, Richie J P Jr: Fasting-induced depletion of glutathione in the aging mouse. Biochem Pharmacol. 1993; 46(2):257-63.
72. Liang W, Menke A L, Driessen A, Koek G H, Lindeman J H, Stoop R, Havekes L M, Kleemann R, van den Hoek A M: Establishment of a general NAFLD scoring system for rodent models and comparison to human liver pathology. PLoS One. 2014; 9(12): e115922.

The invention claimed is:

1. A composition for treatment of and maintaining the health of the liver, comprising a mixture of enriched plant extracts, wherein the mixture of enriched plant extracts consist of at least one enriched *Myristica* extract enriched for one or more lignans, at least one enriched *Astragalus* extract enriched for one or more polysaccharides and triterpenoids, and at least one enriched *Schizandra* extract enriched for one or more lignans and organic acids, wherein the mixture of the at least one *Myristica* extract, the at least one *Astragalus* extract and the at least one *Schizandra* extract is blended in a ratio of 4:16:5, and wherein the one or more organic acids comprises malic acid, citric acid, shikimic acid or a combination thereof.

2. The composition for treatment of and maintaining the health of the liver of claim 1, wherein the one or more lignans comprise phenylpropanoids, dimers, polymers or a combination thereof.

3. The composition of claim 1, wherein the at least one *Myristica* extract comprises 0.01% to 99.9% phenylpropanoids or lignan dimers and polymers.

4. The composition of claim 1, wherein the at least one *Myristica* extract comprises *Myristica fragrans* extract.

5. The composition of claim 1, comprising at least one *Myristica* extract enriched for one or more phenylpropanoids and lignans, wherein the at least one extract is extracted from *Myristica* plants with water, ethanol, methanol, alcohol and water mixed solvents.

6. The composition of claim 1, wherein the at least one *Astragalus* extract comprises *Astragalus membranaceus* extract.

7. The composition of claim 1, wherein the at least one *Astragalus* extract comprises 0.01% to 100% of polysaccharides and 0.01% to 100% triterpenoids.

8. The composition of claim 1, wherein the at least one *Schizandra* extract comprises *Schisandra chinensis* extract.

9. The composition of claim 1, wherein the at least one enriched *Myristica* extract enriched for one or more lignans, at least one enriched *Astragalus* extract enriched for one or more polysaccharides and triterpenoids, and at least one enriched *Schizandra* extract enriched for one or more lignans and organic acids are extracted from the group comprising stems, stem barks, trunks, trunk barks, twigs, tubers, roots, root barks, young shoots, seeds, rhizomes, flowers, fruits, seeds, or leaves.

10. The composition of claim 1, wherein the composition additionally comprises plant powder or plant extract of milk thistle, Aloe, *Artemisia' curcuma*, bupleurum, licorice, *salvia, morus*, hovenia, agrimony, cudrania, lyceum, citrus, *prunus*, yellow mume, dandelion, *vitis*, grape seed, *rubus, camellia*, green tea, krill oil, yeast, soy bean, EGCG, catechins, flavonoids, phospholipids, pycnogenols, gelatins, soy lecithin, pancreatic enzymes, N-acetyl-cysteine, taurine, riboflavin, niacin, pyridoxine, folic acid, carotenes, vitamin A, vitamin B2, B6, and B16, vitamin C, vitamin E, glutathione, branched-chain amino acids, selenium, copper, zinc, manganese, coenzyme Q10, L-arginine, L-glutamine, or phosphatidylcholine.

11. The composition of claim 1, wherein the composition further comprises a pharmaceutically or nutraceutically acceptable carrier, diluent, or excipient, wherein the composition comprises from about 0.5 weight percent (wt %) to about 90 weight percent of active ingredients of the extract mixture.

12. The composition of claim 11, wherein the composition is formulated as a tablet, hard capsule, soft gel capsule, powder, granule, liquid, tincture, sache, ready to drink shot, or lozenge.

13. The composition of claim 1, wherein the composition is administered at a dose of 0.01 to 500 mg/kg of body weight of a human or animal.

* * * * *